United States Patent
Nanko

(10) Patent No.: US 12,275,911 B2
(45) Date of Patent: Apr. 15, 2025

(54) FLUORINE-CONTAINING ETHER COMPOUND, LUBRICANT FOR MAGNETIC RECORDING MEDIUM, AND MAGNETIC RECORDING MEDIUM

(71) Applicant: Resonac Corporation, Tokyo (JP)

(72) Inventor: Masaki Nanko, Tokyo (JP)

(73) Assignee: Resonac Corporation, Tokyo (JP)

( * ) Notice: Subject to any disclaimer, the term of this patent is extended or adjusted under 35 U.S.C. 154(b) by 0 days.

(21) Appl. No.: 18/574,225

(22) PCT Filed: Jun. 27, 2022

(86) PCT No.: PCT/JP2022/025579
§ 371 (c)(1),
(2) Date: Dec. 26, 2023

(87) PCT Pub. No.: WO2023/276954
PCT Pub. Date: Jan. 5, 2023

(65) Prior Publication Data
US 2024/0254403 A1 Aug. 1, 2024

(30) Foreign Application Priority Data
Jun. 29, 2021 (JP) ................................ 2021-107598

(51) Int. Cl.
*C10M 107/38* (2006.01)
*C08G 65/26* (2006.01)
(Continued)

(52) U.S. Cl.
CPC ....... *C10M 107/38* (2013.01); *C08G 65/2639* (2013.01); *C10M 171/04* (2013.01);
(Continued)

(58) Field of Classification Search
CPC .............. C10M 107/38; C10M 171/04; C10M 2213/0606; C10M 2213/003;
(Continued)

(56) References Cited

U.S. PATENT DOCUMENTS

| 11,820,863 | B2 * | 11/2023 | Li | .......................... C08G 65/007 |
| 11,879,109 | B2 * | 1/2024 | Asano | .................. G11B 5/7257 |
| 2021/0155751 | A1 * | 5/2021 | Kato | ..................... C07C 233/25 |

FOREIGN PATENT DOCUMENTS

| JP | 11-131083 A | 5/1999 |
| JP | 2022-024373 A | 2/2022 |

(Continued)

*Primary Examiner* — Cephia D Toomer
(74) *Attorney, Agent, or Firm* — Sughrue Mion, PLLC

(57) ABSTRACT

The present invention provides a fluorine-containing ether compound that can form a lubricating layer which has excellent wear resistance even if the thickness is thin and in which a decrease in film thickness due to spin-off is less likely to occur. The fluorine-containing ether compound is represented by the following formula. $R^1$—$R^2$—O—$CH_2$—$R^3$—$CH_2$—O—$R^4$—$R^5$ ($R^3$ is a perfluoropolyether chain. $R^1$ and $R^5$ are either an alkyl group which may have a substituent or a hydrocarbon group having a double bond or triple bond. $R^2$ and $R^4$ are each a divalent linking group containing one or more heteroatoms, and have one or more polar groups, and the terminal end on the side bonded to $R^1$ and $R^5$ is a heteroatom. At least one of $R^2$ and $R^4$ contains one or more secondary amine structures. At least one of $R^1$—$R^2$— and —$R^4$—$R^5$ contains one or more cyano groups).

17 Claims, 1 Drawing Sheet

(51) Int. Cl.
*C10M 171/04* (2006.01)
*C10N 20/04* (2006.01)
*C10N 40/18* (2006.01)

(52) U.S. Cl.
CPC . *C08G 2650/48* (2013.01); *C10M 2213/0606* (2013.01); *C10N 2020/04* (2013.01); *C10N 2040/18* (2013.01)

(58) Field of Classification Search
CPC ............ C08G 65/2639; C08G 2650/48; C08G 65/007; C08G 65/26; C10N 2020/04; C10N 2040/18; C10N 2030/06; C10N 2050/023; C07C 255/24; G11B 5/725
See application file for complete search history.

(56) References Cited

FOREIGN PATENT DOCUMENTS

| | | |
|---|---|---|
| WO | 2019/039200 A1 | 2/2019 |
| WO | 2019/039265 A1 | 2/2019 |
| WO | 2019/054148 A1 | 3/2019 |
| WO | 2021/054202 A1 | 3/2021 |
| WO | 2021/229338 A1 | 11/2021 |

* cited by examiner

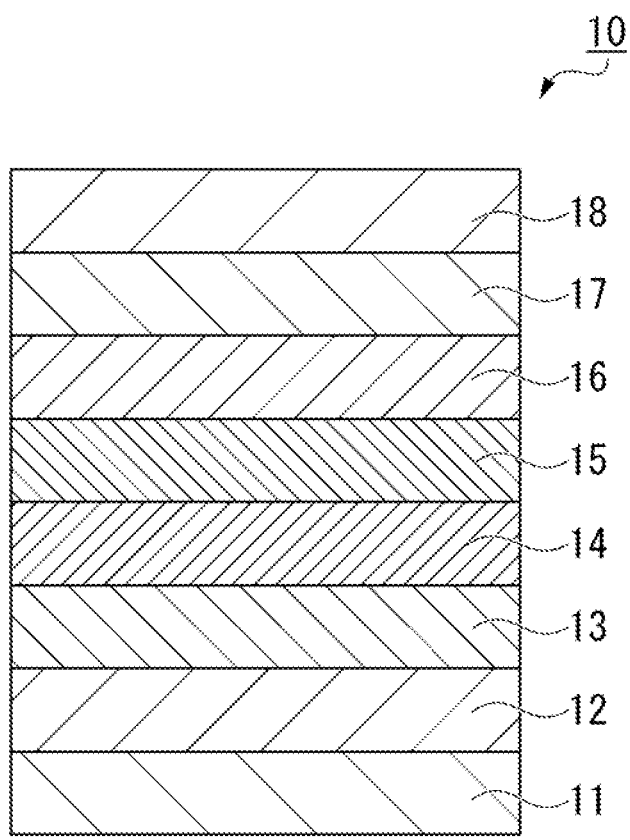

FLUORINE-CONTAINING ETHER COMPOUND, LUBRICANT FOR MAGNETIC RECORDING MEDIUM, AND MAGNETIC RECORDING MEDIUM

TECHNICAL FIELD

The present invention relates to a fluorine-containing ether compound, a lubricant for a magnetic recording medium, and a magnetic recording medium.

This application is a National Stage of International Application No. PCT/JP2022/025579 filed Jun. 27, 2022, claiming priority based on Japanese Patent Application No. 2021-107598, filed Jun. 29, 2021, the content of which is incorporated herein by reference.

BACKGROUND ART

The development of magnetic recording media suitable for high recording densities has progressed in order to improve the recording densities of magnetic recording/reproducing devices.

As a conventional magnetic recording medium, there has been a magnetic recording medium in which a recording layer is formed on a substrate and a protective layer made of carbon or the like is formed on the recording layer. The protective layer protects information recorded in the recording layer and enhances the slidability of a magnetic head. However, sufficient durability of the magnetic recording medium cannot be obtained by simply providing the protective layer on the recording layer. Therefore, generally, a lubricant is applied to the surface of the protective layer to form a lubricating layer.

As a lubricant used when the lubricating layer of the magnetic recording medium is formed, for example, one containing a compound having a polar group such as a hydroxyl group, an amino group, and a cyano group at the terminal of a fluorine polymer having a repeating structure containing $CF_2$ has been proposed.

For example, Patent Document 1 discloses a fluorine-containing ether compound in which a divalent linking group having a polar group is connected to both terminals of a perfluoropolyether chain, and a terminal group in which one or more hydrogen atoms of an organic group having 1 to 8 carbon atoms are substituted with a cyano group is bonded to at least one of the linking groups.

In addition, Patent Document 2 discloses a polyether compound having a structure in which an amino alcohol group is introduced into the terminal of a molecular chain of perfluoropolyether.

In addition, Patent Document 3 discloses a fluorine-containing ether compound in which a linking group that combines an ether bond (—O—), a methylene group (—CH$_2$—), and a methylene group in which one hydrogen atom is substituted with a hydroxyl group (—CH(OH)—) is disposed between the perfluoropolyether chain and both terminal groups.

CITATION LIST

Patent Document

Patent Document 1: PCT International Publication No. WO2019/039200
Patent Document 2: Japanese Unexamined Patent Application, First Publication No. H11-131083
Patent Document 3: PCT International Publication No. WO2019/054148

SUMMARY OF INVENTION

Technical Problem

There is a demand for a further decrease in the floating height of a magnetic head in magnetic recording/reproducing devices. This requires a further decrease in the thickness of a lubricating layer in magnetic recording media. However, generally, if the thickness of the lubricating layer is reduced, the wear resistance of the magnetic recording medium tends to be lowered.

As a method of reducing the film thickness of the lubricating layer while maintaining sufficient wear resistance, it is conceivable to use a lubricant having a small average molecular weight. However, in the lubricating layer formed using the lubricant having a small average molecular weight, spin-off is likely to occur.

In recent years, with a rapid increase in recording density of magnetic recording media, the rotational speed of magnetic recording media has become faster. When a magnetic recording medium is rotated at a high speed, a phenomenon in which the lubricant scatters due to a centrifugal force during rotation or the lubricant evaporates due to heat generated during rotation may occur. This phenomenon is called spin-off.

When spin-off occurs, since the film thickness of the lubricating layer decreases, the wear resistance of the lubricating layer gradually decreases. As a result, in the worst case, damage (head crash) to the magnetic recording medium may occur due to contact with the magnetic head. As a method of preventing the occurrence of spin-off, maintaining the wear resistance of the lubricating layer, and improving the durability of the magnetic recording medium, it is effective to use a lubricant having a large average molecular weight.

The present invention has been made in view of the above circumstances, and an object of the present invention is to provide a fluorine-containing ether compound that can form a lubricating layer which has excellent wear resistance even if the thickness is thin and in which a decrease in film thickness due to spin-off is less likely to occur, and can be suitably used as a material for a lubricant for a magnetic recording medium.

In addition, an object of the present invention is to provide a lubricant for a magnetic recording medium containing the fluorine-containing ether compound of the present invention.

In addition, an object of the present invention is to provide a magnetic recording medium having a lubricating layer containing the fluorine-containing ether compound of the present invention and having excellent reliability and durability.

Solution to Problem

The inventors conducted extensive studies in order to address the above problems.

As a result, it was found that a fluorine-containing ether compound could be used which has a structure in which terminal groups are bonded to both ends of a perfluoropolyether chain via linking groups, at least one of the linking groups disposed at both ends has one or more secondary amine structures (—NH—), and at least one of the structures disposed at both ends in which the linking group and the terminal group are bonded has one or more cyano groups (—CN), and the present invention was completed.

That is, the present invention relates to the following aspects.

[1] A fluorine-containing ether compound represented by the following Formula (1):

$$R^1-R^2-O-CH_2-R^3-CH_2-O-R^4-R^5 \quad (1)$$

(in Formula (1), $R^3$ is a perfluoropolyether chain; $R^1$ and $R^5$ are each independently a terminal group composed of either an alkyl group which may have a substituent or a hydrocarbon group having a double bond or triple bond; $R^2$ and $R^4$ are each a divalent linking group containing one or more heteroatoms and have one or more polar groups, and the terminal end thereof on the side bonded to $R^1$ and $R^5$ is a heteroatom; at least one of $R^2$ and $R^4$ contains one or more secondary amine structures; and at least one of $R^1-R^2-$ and $-R^4-R^5$ contains one or more cyano groups).

[2] The fluorine-containing ether compound according to [1],
wherein the polar groups of $R^2$ and $R^4$ are any one selected from a secondary amine structure, a hydroxyl group and a cyano group.

[3] The fluorine-containing ether compound according to [1],
wherein, in Formula (1), $-R^2-O-$ is represented by the following Formula (2), and $-O-R^4-$ is represented by the following Formula (3):

$$-[A]_a[B]_d-O- \quad (2)$$

$$-O-[C]_g[D]_j- \quad (3)$$

(in Formula (2), [A] is represented by the following Formula (4-1), and [B] is represented by the following Formula (4-2); the order of [A] and [B] in Formula (2) may be interchanged; a is an integer of 0 to 3, d is an integer of 0 to 3, and at least one of a and d is 1 or more; and the terminal —CH$_2$— located on the side opposite to X in Formula (4-1) or the terminal —CH$_2$— located on the side opposite to X in (4-2) is bonded to —O— in Formula (2))

(in Formula (3), [C] is represented by the following Formula (5-1), and [D] is represented by the following Formula (5-2); the order of [C] and [D] in Formula (3) may be interchanged; g is an integer of 0 to 3, j is an integer of 0 to 3, and at least one of g and j is 1 or more; and the terminal —CH$_2$— located on the side opposite to X in Formula (5-1) or the terminal —CH$_2$— located on the side opposite to X in (5-2) is bonded to —O— in Formula (3))

(4-1)

(4-2)

(5-1)

(5-2)

(in Formula (4-1), b and c are each an integer of 0 to 4; in Formula (4-2), e and f are each an integer of 0 to 4; in Formula (5-1), h and i are each an integer of 0 to 4; in Formula (5-2), k and l are each an integer of 0 to 4; in Formulae (4-1), (4-2), (5-1), and (5-2), X is O or NH; and one or more of X's in Formulae (4-1), (4-2), (5-1), and (5-2) are NH).

[4] The fluorine-containing ether compound according to any one of [1] to [3],
wherein the number of secondary amine structures contained in a molecule thereof is 2 or more.

[5] The fluorine-containing ether compound according to any one of [1] to [4],
wherein the number of hydroxyl groups contained in a molecule thereof is 3 or less.

[6] The fluorine-containing ether compound according to any one of [1] to [5],
wherein the number of cyano groups contained in a molecule thereof is 3 or less.

[7] The fluorine-containing ether compound according to any one of [1] to [6],
wherein the total number of secondary amine structures, hydroxyl groups and cyano groups contained in the molecule is 8 or less.

[8] The fluorine-containing ether compound according to any one of [1] to [7],
wherein the number of secondary amine structures contained in a molecule thereof is 2 or more, the number of hydroxyl groups is 3 or less, the number of cyano groups is 3 or less, and the total number of secondary amine structures, hydroxyl groups and cyano groups is 8 or less.

[9] The fluorine-containing ether compound according to any one of [1] to [8],
wherein $-R^2-O-$ in Formula (1) is any of the following Formulae (11-1) to (11-12):

(11-1)

(11-2)

(11-3)

-continued

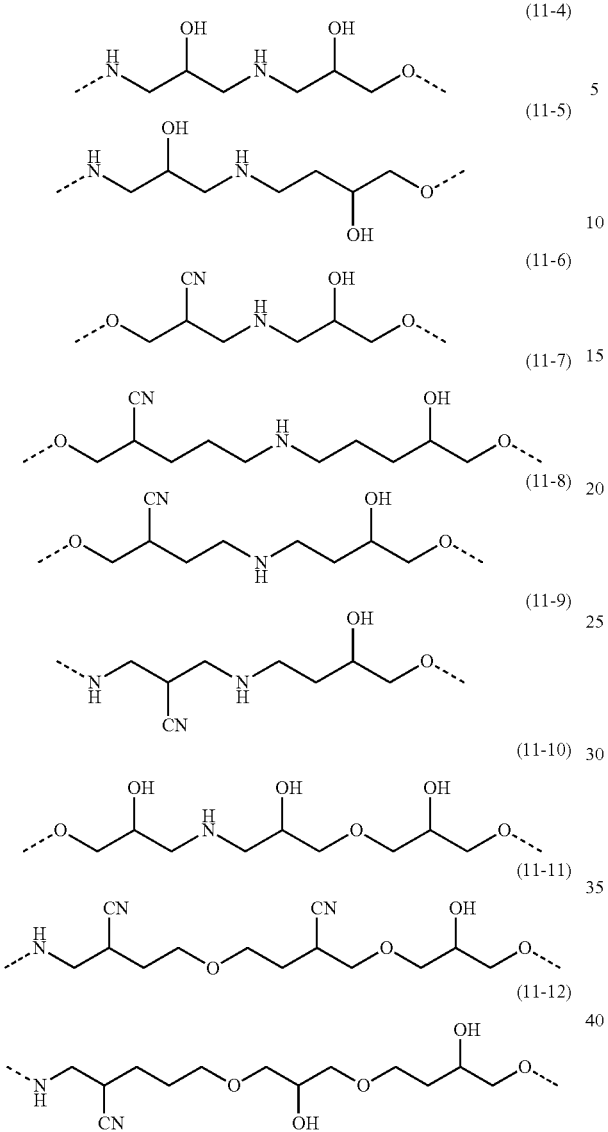

[10] The fluorine-containing ether compound according to any one of [1] to [9],
wherein the alkyl group which may have a substituent is an alkyl group having a hydroxyl group or cyano group.

[11] The fluorine-containing ether compound according to any one of [1] to [10],
wherein the hydrocarbon group having a double bond or triple bond is any of a group containing an aromatic hydrocarbon, a group containing an aromatic heterocycle, an alkenyl group, and an alkynyl group.

[12] The fluorine-containing ether compound according to any one of [1] to [11],
wherein $R^3$ in Formula (1) is any of the following Formulae (6) to (10):

(in Formula (6), m and n indicate average degrees of polymerization, and each represent 0.1 to 30)

(in Formula (7), w indicates the average degree of polymerization, and is 0.1 to 30)

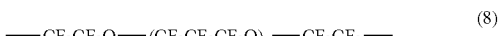

(in Formula (8), x indicates the average degree of polymerization, and is 0.1 to 30)

(in Formula (9), y indicates the average degree of polymerization, and is 0.1 to 30).

(in Formula (10), z indicates the average degree of polymerization, and is 0.1 to 30).

[13] The fluorine-containing ether compound according to [1], wherein the compound represented by Formula (1) is any one of compounds represented by the following Formulae (A), (J), (P), (Q) and (U):

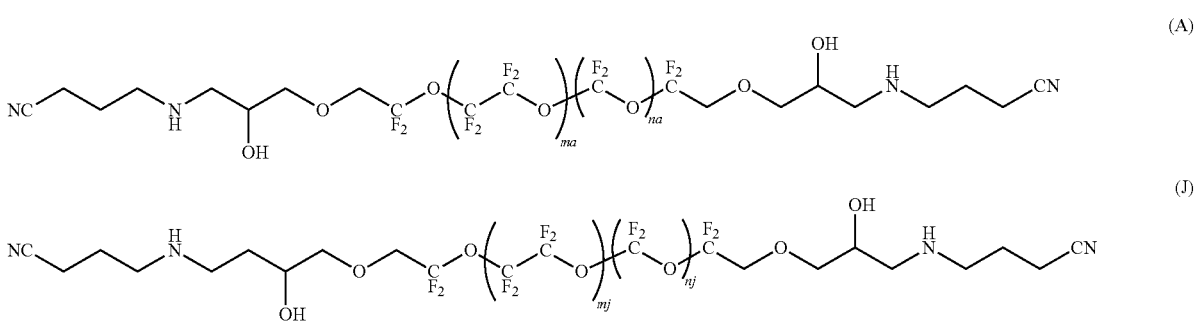

-continued

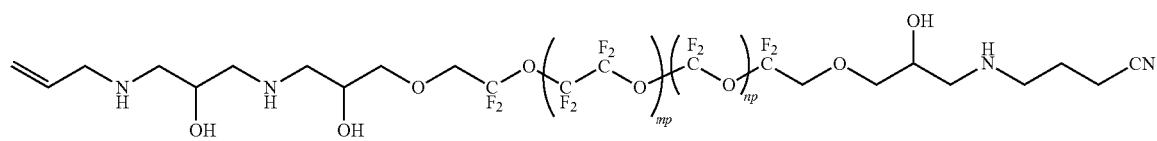

(in Formula (A), ma and na indicate average degrees of polymerization, ma is 1 to 30, and na is 0.1 to 30)
(in Formula (J), mj and nj indicate average degrees of polymerization, mj is 1 to 30, and nj is 0.1 to 30)
(in Formula (P), mp and np indicate average degrees of polymerization, mp is 1 to 30, and np is 0.1 to 30)

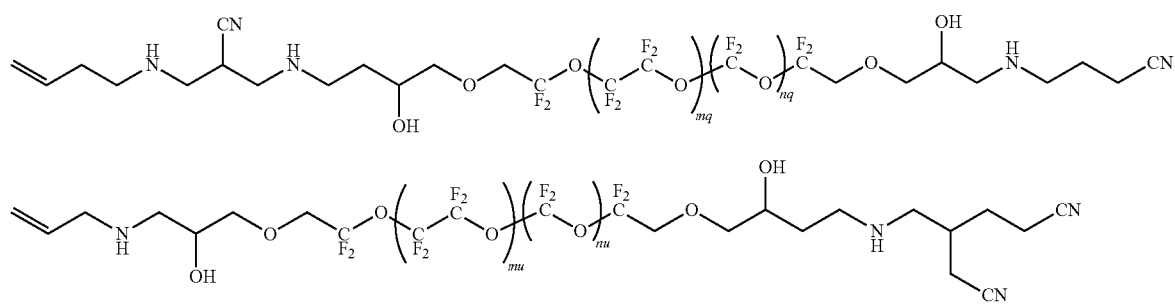

(in Formula (Q), mq and nq indicate average degrees of polymerization, mq is 1 to 30, and nq is 0.1 to 30)
(in Formula (U), mu and nu indicate average degrees of polymerization, mu is 1 to 30, and nu is 0.1 to 30).

[14] The fluorine-containing ether compound according to any one of [1] to [13],
wherein the number-average molecular weight is in a range of 500 to 10,000.

[15] A lubricant for a magnetic recording medium, which contains the fluorine-containing ether compound according to any one of [1] to [14].

[16] A magnetic recording medium in which at least a magnetic layer, a protective layer and a lubricating layer are sequentially provided on a substrate,
wherein the lubricating layer contains the fluorine-containing ether compound according to any one of [1] to [14].

[17] The magnetic recording medium according to [16],
wherein the lubricating layer has an average film thickness of 0.5 nm to 2.0 nm.

Advantageous Effects of Invention

The fluorine-containing ether compound of the present invention is the compound represented by Formula (1) and suitable as a material for a lubricant for a magnetic recording medium.

Since the lubricant for a magnetic recording medium of the present invention includes the fluorine-containing ether compound of the present invention, it is possible to form a lubricating layer which has excellent wear resistance even if the thickness is thin and in which a decrease in film thickness due to spin-off is less likely to occur.

The magnetic recording medium of the present invention has excellent reliability and durability because a lubricating layer containing the fluorine-containing ether compound of the present invention and having excellent wear resistance and spin-off resistance is provided.

BRIEF DESCRIPTION OF DRAWINGS

The FIGURE is a schematic cross-sectional view showing an example of a magnetic recording medium according to one embodiment of the present invention.

DESCRIPTION OF EMBODIMENTS

Hereinafter, preferable examples of a fluorine-containing ether compound, a lubricant for a magnetic recording medium (hereinafter abbreviated as a "lubricant" in some cases) and a magnetic recording medium of the present invention will be described in detail. Here, the present invention is not limited only to the following embodiments.

The present invention is not limited only to the following examples, and numbers, amounts, ratios, compositions, types, positions, materials, configurations and the like can be added, omitted, substituted, and changed without departing from the spirit and scope of the present invention.

[Fluorine-Containing Ether Compound]

The fluorine-containing ether compound of the present embodiment is represented by the following Formula (1).

(in Formula (1), $R^3$ is a perfluoropolyether chain; $R^1$ and $R^5$ are each independently a terminal group composed of either an alkyl group which may have a substituent or a hydrocarbon group having a double bond or triple bond; $R^2$ and $R^4$ are each a divalent linking group containing one or more heteroatoms and have one or more polar groups, and the terminal end thereof on the side bonded to $R^1$ and $R^5$ is a heteroatom; at least one of $R^2$ and $R^4$ contains one or more secondary amine structures; and at least one of $R^1$—$R^2$— and —$R^4$—$R^5$ contains one or more cyano groups).

Here, the reason why excellent wear resistance and spin-off resistance are obtained even if the thickness is thin when a lubricating layer is formed on the protective layer of the magnetic recording medium using the lubricant containing the fluorine-containing ether compound of the present embodiment will be described.

The fluorine-containing ether compound of the present embodiment has a perfluoropolyether chain (hereinafter abbreviated as a "PFPE chain" in some case) represented by $R^3$ as shown in Formula (1). In a lubricating layer containing the fluorine-containing ether compound of the present embodiment, the PFPE chain covers the surface of the protective layer, imparts lubricity to the lubricating layer, and reduces the frictional force between the magnetic head and the protective layer.

In addition, in the fluorine-containing ether compound represented by Formula (1), $R^2$ and $R^4$ are each a divalent linking group containing one or more heteroatoms and have one or more polar groups. In addition, at least one of $R^2$ and $R^4$ contains one or more secondary amine structures (—NH—). In the lubricant containing the fluorine-containing ether compound of the present embodiment, the polar groups contained in $R^2$ and $R^4$ and the secondary amine structure which is a polar group contained in at least one of $R^2$ and $R^4$ cause the fluorine-containing ether compound and the protective layer to come into close contact with each other and improve wear resistance.

The secondary amine structure (—NH—) of the fluorine-containing ether compound represented by Formula (1) has a polarity and has an interaction (affinity) with the protective layer and an intramolecular interaction. The interaction of the secondary amine structure with respect to the protective layer is the same as that of a hydroxyl group. However, the intramolecular interaction of the secondary amine structure is weaker than that of a hydroxyl group. Therefore, in —NH— contained in the fluorine-containing ether compound represented by Formula (1) on the protective layer, the interaction with the surface of the protective layer has priority over the intramolecular interaction. As a result, the fluorine-containing ether compound represented by Formula (1) is less likely to aggregate on the protective layer and can form a thin lubricating layer with a sufficient coverage, compared with a fluorine-containing ether compound which has, in place of the —NH—'s, the same number of hydroxyl groups as the number of —NH—'s which are contained in the fluorine-containing ether compound represented by Formula (1). Accordingly, when the lubricant containing the fluorine-containing ether compound represented by Formula (1) is used, a lubricating layer having excellent wear resistance is obtained.

In addition, at least one of $R^1$—$R^2$— and —$R^4$—$R^5$ in Formula (1) has one or more cyano groups. Cyano groups have a rigid C≡N bond, and have a low degree of freedom and thus the intramolecular interaction thereof is weaker than that of hydroxyl groups. In addition, since the cyano group has a nitrogen atom, it exhibits an interaction with the protective layer. Therefore, in the cyano group contained in the fluorine-containing ether compound represented by Formula (1) on the protective layer, the interaction with the surface of the protective layer has priority over the intramolecular interaction. As a result, compared with a fluorine-containing ether compound which has, in place of the cyano groups, the same number of hydroxyl groups as the number of cyano groups which are contained in the fluorine-containing ether compound represented by Formula (1), the fluorine-containing ether compound represented by Formula (1) is less likely to aggregate on the protective layer and a thin lubricating layer can be formed with a sufficient coverage.

In addition, since the fluorine-containing ether compound represented by Formula (1) contains one or more secondary amine structures and one or more cyano groups, very strong adhesion to the protective layer is obtained due to a synergistic effect of the secondary amine structure and the cyano group. Therefore, the fluorine-containing ether compound represented by Formula (1) can form a lubricating layer in which the occurrence of spin-off is prevented compared with, for example, a fluorine-containing ether compound that does not contain one or both of a secondary amine structure and a cyano group.

As described above, when the lubricant containing the fluorine-containing ether compound of the present embodiment is used to form a lubricating layer on the protective layer of the magnetic recording medium, excellent wear resistance and spin-off resistance are obtained even if the thickness is thin.

($R^2$, $R^4$)

In Formula (1), $R^2$ and $R^4$ are each a divalent linking group containing one or more heteroatoms and have one or more polar groups. At least one of $R^2$ and $R^4$ contains one or more secondary amine structures (—NH—). This is because the fluorine-containing ether compound that can form a lubricating layer having excellent wear resistance is obtained.

Examples of polar groups contained in $R^2$ and $R^4$ include a hydroxyl group, alkoxy group, amide group, amino group, carbonyl group, carboxy group, nitro group, cyano group, sulfo group, and secondary amine structure. An ether bond (—O—) is not included among the polar groups for $R^2$ and $R^4$. Among these, the polar groups of $R^2$ and $R^4$ are preferably one selected from among a secondary amine structure, a hydroxyl group and a cyano group. This is because the fluorine-containing ether compound that can form a lubricating layer with even better adhesion to the protective layer is obtained.

The number of polar groups contained in each of $R^2$ and $R^4$ is preferably 1 to 6 and more preferably 1 to 4. Since the number of polar groups contained in each of $R^2$ and $R^4$ is 1 or more, the fluorine-containing ether compound that can form a lubricating layer having favorable adhesion to the protective layer and having excellent wear resistance is obtained. When the number of polar groups contained in each of $R^2$ and $R^4$ is 6 or less, it is possible to prevent the occurrence of pickup in which the polarity of the fluorine-containing ether compound becomes too strong and the compound adheres as foreign matter (smear) to a magnetic head.

$R^2$ and $R^4$ are each preferably a linking group having 1 to 15 carbon atoms, and more preferably a linking group having 3 to 12 carbon atoms. This is because, when the number of carbon atoms of $R^2$ and $R^4$ is 1 to 15, the fluorine-containing ether compound in which the proportion of fluorine atoms in the entire molecule is appropriate and which can form a lubricating layer having excellent lubricity is obtained. However, the number of carbon atoms in the linking group represented by $R^2$ and $R^4$ does not include the number of carbon atoms in the polar group.

Examples of heteroatoms contained in $R^2$ and $R^4$ include an oxygen atom, nitrogen atom, sulfur atom, phosphorus atom, and boron atom, and an oxygen atom and/or nitrogen atom is preferable.

In $R^2$, the terminal end on the side bonded to $R^1$ is a heteroatom. The heteroatom in $R^2$ which is bonded to $R^1$ is preferably an oxygen atom or a nitrogen atom.

In $R^4$, the terminal end on the side bonded to $R^5$ is a heteroatom. The heteroatom in $R^4$ which is bonded to $R^5$ is preferably an oxygen atom or a nitrogen atom.

When $R^2$ and/or $R^4$ contains an oxygen atom which is a heteroatom in the main chain, it is preferable that the oxygen atom form an ether bond (—O—). This is because, in addition to imparting appropriate flexibility to the fluorine-containing ether compound, the affinity between the polar group of the linking group represented by $R^2$ and/or $R^4$ and the protective layer is increased, and the fluorine-containing ether compound that can form a lubricating layer with even better adhesion to the protective layer is obtained.

When $R^2$ and/or $R^4$ contains a nitrogen atom which is a heteroatom in the main chain, it is preferable that the nitrogen atom form a secondary amine structure (—NH—). This is because the fluorine-containing ether compound that can form a lubricating layer having excellent wear resistance is obtained.

In order to impart appropriate flexibility to the entire molecule, the linking group represented by $R^2$ and $R^4$ is preferably one in which groups selected from among a methylene group (—CH$_2$—), a methylene group substituted with a hydroxyl group or a cyano group (—CHY—; Y represents a hydroxyl group or a cyano group), —O—, and —NH— are bonded in any number or order.

In Formula (1), preferably, —R$^2$—O— is represented by the following Formula (2), and —O—R$^4$— is represented by the following Formula (3).

$$—[A]_a[B]_d—O— \quad (2)$$

$$—O—[C]_g[D]_j— \quad (3)$$

(in Formula (2), [A] is represented by the following Formula (4-1), and [B] is represented by the following Formula (4-2); the order of [A] and [B] in Formula (2) may be interchanged; a is an integer of 0 to 3, d is an integer of 0 to 3, at least one of a and d is 1 or more; and the terminal —CH$_2$— on the side opposite to X in Formula (4-1) or the terminal —CH$_2$— on the side opposite to X in (4-2) is bonded to —O— in Formula (2)).

(in Formula (3), [C] is represented by the following Formula (5-1), and [D] is represented by the following Formula (5-2); the order of [C] and [D] in Formula (3) may be interchanged; g is an integer of 0 to 3, j is an integer of 0 to 3, and at least one of g and j is 1 or more; and the terminal —CH$_2$— on the side opposite to X in Formula (5-1) or the terminal —CH$_2$— on the side opposite to X in (5-2) is bonded to —O— in Formula (3)).

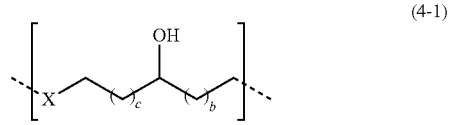

(4-1)

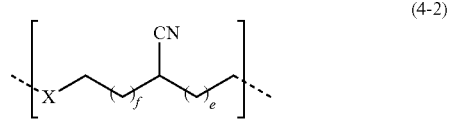

(4-2)

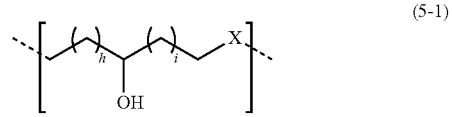

(5-1)

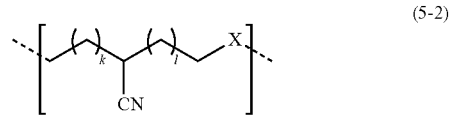

(5-2)

(in Formula (4-1), b and c are each an integer of 0 to 4; in Formula (4-2), e and f are each an integer of 0 to 4; in Formula (5-1), h and i are each an integer of 0 to 4; in Formula (5-2), k and l are each an integer of 0 to 4; in Formulae (4-1), (4-2), (5-1), and (5-2), X is O or NH; and one or more of X's in Formulae (4-1), (4-2), (5-1), and (5-2) are NH).

In Formula (2), [A] is represented by Formula (4-1), and [B] is represented by Formula (4-2). The terminal —CH$_2$— on the side opposite to X in Formula (4-1) or the terminal —CH$_2$— on the side opposite to X in (4-2) is bonded to —O— in Formula (2). In Formula (2), a is an integer of 0 to 3, d is an integer of 0 to 3, at least one of a and d is 1 or more. That is, Formula (2) includes at least one of [A] and [B].

The order of [A] and [B] in Formula (2) may be interchanged. When a is 2 or more and d is 1 or more in Formula (2), or when d is 2 or more and a is 1 or more in Formula (2), the arrangement order of [A] and [B] in Formula (2) is not particularly limited.

In Formula (2), since at least one of a and d is 1 or more, a fluorine-containing ether compound that can form a lubricating layer with favorable adhesion to the protective layer is obtained. The sum of a and d in Formula (2) is 6 or less, preferably 4 or less, and more preferably 2 or less. When the sum of a and d in Formula (2) is 6 or less, this is preferable because it is possible to prevent the occurrence of pickup in which the polarity of the fluorine-containing ether compound becomes too high and the compound adheres as foreign matter (smear) to a magnetic head.

When a in Formula (2) is 2 or more, combinations of b and c in each repeating unit (—X—CH$_2$—(CH$_2$)$_c$—CH(OH)—(CH$_2$)$_b$—CH$_2$—) represented by Formula (4-1) may be the same as or different from each other.

When d in Formula (2) is 2 or more, combinations of e and f in each repeating unit (—X—CH$_2$—(CH$_2$)$_f$—CH(CN)—(CH$_2$)$_e$—CH$_2$—) represented by Formula (4-2) may be the same as or different from each other.

b and c in Formula (4-1) and e and f in Formula (4-2) are each an integer of 0 to 4 and preferably an integer of 0 to 3. In addition, the sum of b and c in Formula (4-1) and the sum of e and f in Formula (4-2) are preferably 0 to 4. When the sum of b and c in Formula (4-1) and the sum of e and f in Formula (4-2) are each 0 to 4, this is preferable because the distance between $R^1$ and the polar group in Formula (4-1) and Formula (4-2) and/or the distance between the polar groups in Formula (4-1) and Formula (4-2) is appropriate.

In the fluorine-containing ether compound of the present embodiment, —R$^2$—O— in Formula (1) can be appropriately selected depending on the performance required for the lubricant containing a fluorine-containing ether compound and the like.

—R$^2$—O— (-[A]$_a$-[B]$_d$—O— shown in Formula (2)) in Formula (1) is preferably one represented by the following Formulae (11-1) to (11-12). When —R$^2$—O— in Formula (1) is one represented by Formulae (11-1) to (11-12), a fluorine-containing ether compound that can form a lubricating layer with better adhesion to the protective layer is obtained. In the structures represented by Formulae (11-1) to (11-12), $R^1$ is bonded to the heteroatom (oxygen atom or nitrogen atom) disposed on the leftmost side (closest to $R^1$) in $R^2$.

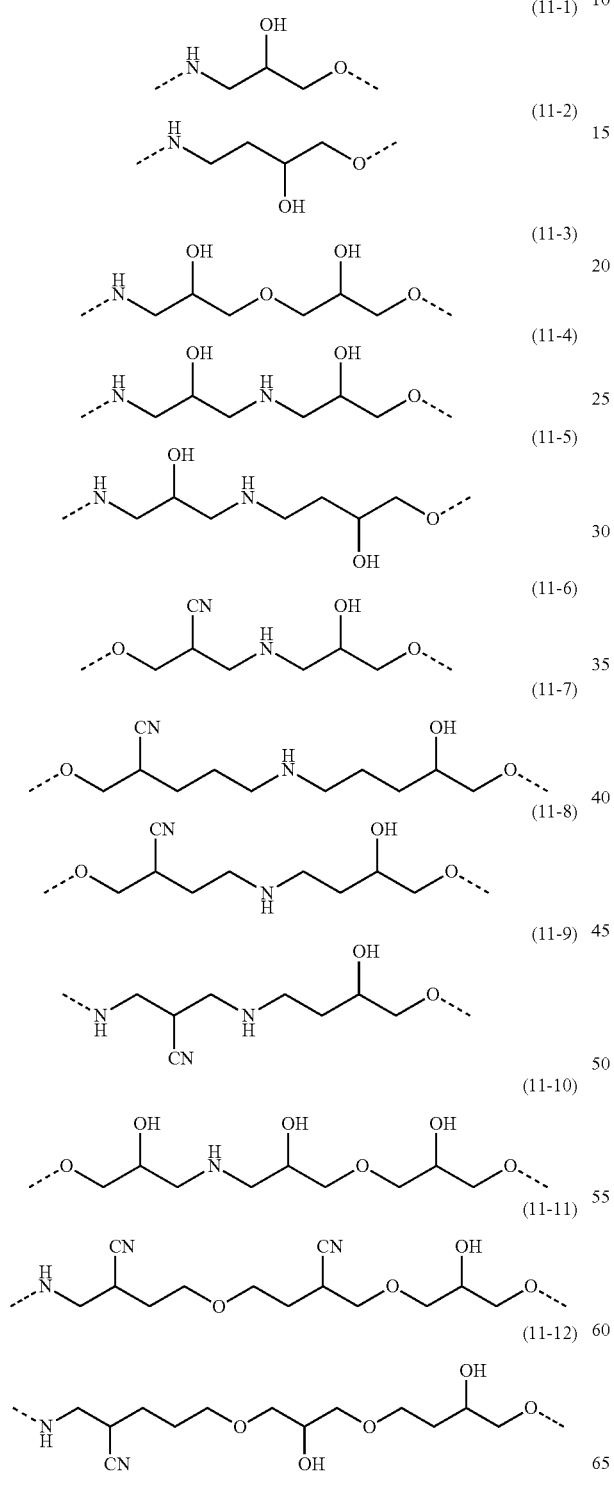

In Formula (3), [C] is represented by Formula (5-1), and [D] is represented by Formula (5-2). The terminal —$CH_2$— on the side opposite to X in Formula (5-1) or the terminal —$CH_2$— on the side opposite to X in (5-2) is bonded to —O— in Formula (3). In Formula (3), g is an integer of 0 to 3, j is an integer of 0 to 3, and at least one of g and j is 1 or more. That is, Formula (3) includes at least one of [C] and [D].

The order of [C] and [D] in Formula (3) may be interchanged. When g is 2 or more and j is 1 or more in Formula (3) or when j is 2 or more and g is 1 or more in Formula (3), the arrangement order of [C] and [D] in Formula (3) is not particularly limited.

In Formula (3), since at least one of g and j is 1 or more, a fluorine-containing ether compound that can form a lubricating layer with favorable adhesion to the protective layer is obtained. The sum of g and j in Formula (3) is 6 or less, preferably 4 or less, and more preferably 2 or less. When the sum of g and j in Formula (3) is 6 or less, this is preferable because it is possible to prevent the occurrence of pickup in which the polarity of the fluorine-containing ether compound becomes too high and the compound adheres as foreign matter (smear) to a magnetic head.

When g in Formula (3) is 2 or more, combinations of h and i in each repeating unit (—$CH_2$—$(CH_2)_h$—$CH(OH)$—$(CH_2)_i$—$CH_2$—X—) represented by Formula (5-1) may be the same as or different from each other.

When j in Formula (3) is 2 or more, combinations of k and l in each repeating unit (—$CH_2$—$(CH_2)_k$—$CH(CN)$—$(CH_2)_l$—$CH_2$—X—) represented by Formula (5-2) may be the same as or different from each other.

h and i in Formula (5-1) and k and l in Formula (5-2) are each an integer of 0 to 4 and preferably an integer of 0 to 3. In addition, the sum of h and i in Formula (5-1) and the sum of k and l in Formula (5-2) are each preferably 0 to 4. When the sum of h and i in Formula (5-1) and the sum of k and l in Formula (5-2) are each 0 to 4, this is preferable because the distance between $R^5$ and the polar group in Formula (5-1) and Formula (5-2) and/or the distance between the polar groups in Formula (5-1) and Formula (5-2) is appropriate.

In the fluorine-containing ether compound of the present embodiment, —O—$R^4$— in Formula (1) can be appropriately selected depending on the performance required for the lubricant containing a fluorine-containing ether compound and the like.

—O—$R^4$— (—O—$[C]_g$-$[D]_j$- shown in Formula (3)) in Formula (1) is preferably any one of the formulae represented by the following Formulae (12-1) to (12-12). When —O—$R^4$— in Formula (1) is one represented by Formulae (12-1) to (12-12), a fluorine-containing ether compound that can form a lubricating layer with better adhesion to the protective layer is obtained. In the structures represented by Formulae (12-1) to (12-12), $R^5$ is bonded to the heteroatom (oxygen atom or nitrogen atom) disposed on the rightmost side (closest to $R^5$) in $R^4$.

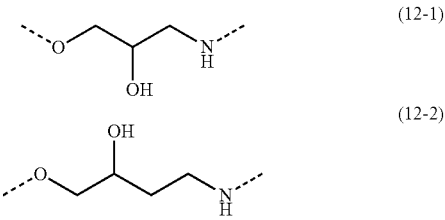

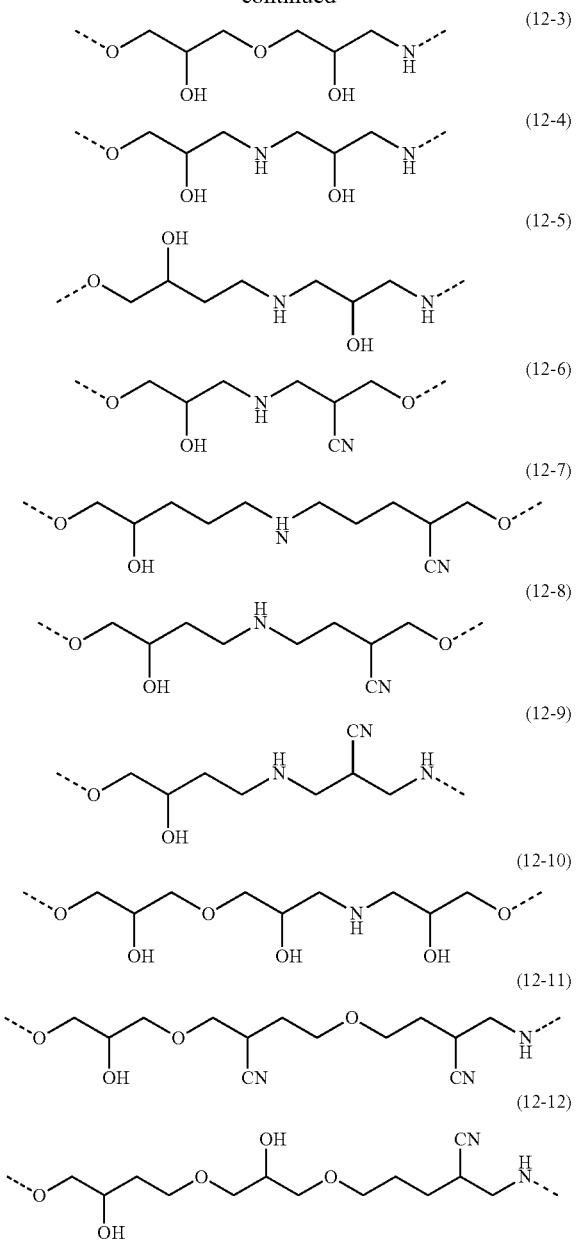

($R^1$, $R^5$)

In the fluorine-containing ether compound represented by Formula (1) according to the present embodiment, $R^1$ represents a terminal group bonded to $R^2$, and $R^5$ represents a terminal group bonded to $R^4$. $R^1$ and $R^5$ each independently represent any of an alkyl group which may have a substituent, and a hydrocarbon group having a double bond or triple bond. In $R^1$ and $R^5$, the terminal end thereof on the side bonded to $R^2$ and $R^4$ is a carbon atom.

In the fluorine-containing ether compound represented by Formula (1), when neither of the linking groups represented by $R^2$ and $R^4$ contains a cyano group, at least one of $R^1$ and $R^5$ has a cyano group as a substituent.

When $R^1$ and/or $R^5$ is an alkyl group which may have a substituent, the alkyl group is preferably an alkyl group having 1 to 8 carbon atoms and more preferably an alkyl group having 1 to 6 carbon atoms. Specific examples thereof include a methyl group, ethyl group, propyl group, butyl group, pentyl group, hexyl group, heptyl group, and octyl group, which may be linear or have a branch.

Examples of substituents in the alkyl group which may have a substituent include a halogeno group, alkoxy group, hydroxyl group, and cyano group, and a hydroxyl group or a cyano group is preferable. When the alkyl group which may have a substituent has these substituents, a fluorine-containing ether compound that can form a lubricating layer having better wear resistance is obtained.

In the present embodiment, at least one of $R^1$ and $R^5$ is preferably an alkyl group having a cyano group so that the fluorine-containing ether compound that can form a lubricating layer having better wear resistance is obtained.

As an alkyl group having a halogeno group as a substituent, an alkyl group having at least one fluoro group is preferable. Examples of alkyl groups having a fluoro group include a trifluoromethyl group, perfluoroethyl group, perfluoropropyl group, perfluorobutyl group, perfluoropentyl group, perfluorohexyl group, octafluoropentyl group, and tridecafluorooctyl group.

As an alkyl group having a hydroxyl group as a substituent, an alkyl group having a hydroxyl group and having 1 to 6 carbon atoms is preferable, and an alkyl group represented by the following Formula (13-1) is more preferable.

(13-1)

(in Formula (13-1), $R^6$ is an alkyl group having 1 to 4 carbon atoms or a hydrogen atom, and p is an integer of 1 to 6).

In Formula (13-1), $R^6$ is an alkyl group having 1 to 4 carbon atoms or a hydrogen atom, and preferably a hydrogen atom. In the structure represented by Formula (13-1), the left side is bonded to $R^2$ or $R^4$. In Formula (13-1), p is an integer of 1 to 6, and is preferably an integer of 1 to 4, and more preferably 2 or 3. When p is 2 or more, $R^6$'s in the repeating unit (—CH($R^6$)—) may be different from each other, or some or all of them may be the same. When the number of carbon atoms in Formula (13-1) (the total number of carbon atoms contained in $R^6$ and p) is 1 to 6, this is preferable because there is no decrease in the surface free energy of the entire molecule due to a low proportion of fluorine atoms in the fluorine-containing ether compound molecule.

As an alkyl group having a cyano group as a substituent, an alkyl group having a cyano group and having 1 to 6 carbon atoms is preferable, and an alkyl group represented by the following Formula (13-2) is more preferable.

(13-2)

(in Formula (13-2), $R^6$ is an alkyl group having 1 to 4 carbon atoms or a hydrogen atom, and q is an integer of 1 to 6).

In Formula (13-2), $R^6$ is an alkyl group having 1 to 4 carbon atoms or a hydrogen atom, and preferably a hydrogen atom. In the structure represented by Formula (13-2), the left side is bonded to $R^2$ or $R^4$. In Formula (13-2), q is an integer of 1 to 6, and is preferably an integer of 1 to 4, and more preferably 2 or 3. If q is 2 or more, $R^6$'s in the repeating unit (—CH($R^6$)—) may be different from each other, or some or all of them may be the same. When the number of carbon atoms in Formula (13-2) (the total number of carbon atoms contained in $R^6$ and q) is 1 to 6, this is preferable because there is no decrease in the surface free energy of the entire molecule due to a low proportion of fluorine atoms in the fluorine-containing ether compound molecule.

An alkyl group having a cyano group as a substituent may have two or more cyano groups. Examples of alkyl groups having two cyano groups include a 5-cyano-3-(cyanomethyl)pentyl group, 4-cyano-1-(cyanomethyl)butyl group, 4-cyano-2-(cyanomethyl)butyl group, 4-cyano-3-(cyanomethyl)butyl group, 4-cyano-1-(cyanoethyl)butyl group, 4-cyano-2-(cyanoethyl)butyl group, 3-cyano-1-(cyanomethyl)propyl group, 3-cyano-2-(cyanomethyl)propyl group, 3-cyano-1-(cyanoethyl)propyl group, and 2-cyano-1-(cyanomethyl)ethyl group.

The hydrocarbon group having a double bond or triple bond as $R^1$ and/or $R^5$ is a hydrocarbon group having at least one double bond or triple bond. The double bond may be either an ethylenic double bond or an aromatic double bond. Examples of hydrocarbon groups having a double bond or triple bond include a group containing an aromatic hydrocarbon, a group containing an aromatic heterocycle, an alkenyl group, and an alkynyl group. The hydrocarbon group having a double bond or triple bond may have a substituent such as an alkyl group, alkoxy group, hydroxyl group, mercapto group, carboxy group, carbonyl group, amino group, cyano group, and halogeno group. Specific examples of hydrocarbon groups having a double bond or triple bond include a phenyl group, methoxyphenyl group, fluorinated phenyl group, naphthyl group, phenethyl group, methoxyphenethyl group, fluorinated phenethyl group, benzyl group, methoxybenzyl group, naphthyl methyl group, methoxynaphthyl group, pyrrolyl group, pyrazolyl group, methylpyrazolylmethyl group, imidazolyl group, furyl group, furfuryl group, oxazolyl group, isoxazolyl group, thienyl group, thienylethyl group, thiazolyl group, methylthiazolylethyl group, isothiazolyl group, pyridyl group, pyrimidinyl group, pyridazinyl group, pyrazinyl group, indolinyl group, benzofuranyl group, benzothienyl group, benzimidazolyl group, benzoxazolyl group, benzothiazolyl group, benzopyrazolyl group, benzoisooxazolyl group, benzisothiazolyl group, quinolyl group, isoquinolyl group, quinazolinyl group, quinoxalinyl group, phthalazinyl group, cinnolinyl group, vinyl group, allyl group, butenyl group, 1-propynyl group, propargyl group (2-propynyl group), butynyl group, methylbutynyl group, pentynyl group, methylpentynyl group, and hexynyl group.

Among the above examples, particularly, the hydrocarbon group having a double bond or triple bond is preferably any of a phenyl group, methoxyphenyl group, thienylethyl group, butenyl group, allyl group, propargyl group, phenethyl group, methoxyphenethyl group, and fluorinated phenethyl group, and more preferably a phenyl group, thienylethyl group, allyl group, or butenyl group. When the hydrocarbon group having a double bond or triple bond is any of a phenyl group, thienylethyl group, allyl group, and butenyl group, a fluorine-containing ether compound that can form a lubricating layer having better wear resistance is obtained.

($R^3$)

In the fluorine-containing ether compound represented by Formula (1) according to the present embodiment, $R^3$ represents a perfluoropolyether chain (PFPE chain). $R^3$ is not particularly limited, and can be appropriately selected depending on the performance required for the lubricant containing a fluorine-containing ether compound and the like. Examples of PFPE chains include a perfluoromethylene oxide polymer, a perfluoroethylene oxide polymer, a perfluoro-n-propylene oxide polymer, a perfluoroisopropylene oxide polymer, and a copolymer thereof.

The PFPE chain may have, for example, a structure represented by the following Formula (Rf) derived from a perfluoroalkylene oxide polymer or copolymer.

(in Formula (Rf), p2, p3, p4, and p5 indicate average degrees of polymerization, and each independently represent 0 to 30; provided that p2, p3, p4, and p5 are not all 0 at the same time; p1 and p6 are average values indicating the number of —$CF_2$—'s, and each independently represent 1 to 3; and the arrangement order of repeating units in Formula (Rf) is not particularly limited).

In Formula (Rf), p2, p3, p4, and p5 indicate average degrees of polymerization, and are each independently 0 to 30, preferably 0 to 20, and more preferably 0 to 15.

In Formula (Rf), p1 and p6 are average values indicating the number of —$CF_2$-'s and each independently represent 1 to 3. p1 and p6 are determined according to the structure of repeating units disposed at the ends of the chain structure in the polymer represented by Formula (Rf).

In Formula (Rf), ($CF_2O$), ($CF_2CF_2O$), ($CF_2CF_2CF_2O$), and ($CF_2CF_2CF_2CF_2O$) are repeating units. The arrangement order of repeating units in Formula (Rf) is not particularly limited. In addition, the number of types of repeating units in Formula (Rf) is not particularly limited.

In Formula (1), $R^3$ is preferably, for example, a PFPE chain represented by the following Formula (Rf-1).

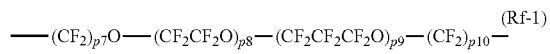

(in Formula (Rf-1), p8 and p9 indicate average degrees of polymerization, and each independently represent 0.1 to 30; and p7 and p10 are average values indicating the number of —$CF_2$—'s and each independently represent 1 to 2).

The arrangement order of repeating units ($CF_2CF_2O$) and ($CF_2CF_2CF_2O$) in Formula (Rf-1) is not particularly limited. Formula (Rf-1) may include any of a random copolymer, a block copolymer, and an alternating copolymer composed of monomer units ($CF_2CF_2O$) and ($CF_2CF_2CF_2O$). In Formula (Rf-1), p8 and p9 indicating average degrees of polymerization are each independently 0.1 to 30, preferably 0.1 to 20, and more preferably 1 to 15. In Formula (Rf-1), p7 and p10 are average values indicating the number of —$CF_2$—'s and each independently represent 1 to 2. p7 and p10 are determined according to the structure or the like of repeating units disposed at the ends of the chain structure in the polymer represented by Formula (Rf-1).

In Formula (1), $R^3$ is preferably any of the following Formulae (6) to (10). Here, the arrangement order of repeating units ($CF_2CF_2O$) and ($CF_2O$) in Formula (6) is not particularly limited. Formula (6) may include any of a random copolymer, a block copolymer, and an alternating copolymer composed of monomer units ($CF_2$—$CF_2$—O) and ($CF_2$—O).

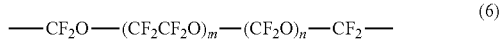

(in Formula (6), m and n indicate average degrees of polymerization, and each represent 0.1 to 30).

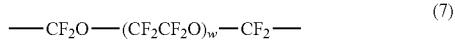

(in Formula (7), w indicates the average degree of polymerization, and is 0.1 to 30).

(in Formula (8), x indicates the average degree of polymerization, and is 0.1 to 30).

(in Formula (9), y indicates the average degree of polymerization, and is 0.1 to 30).

(in Formula (10), z indicates the average degree of polymerization, and is 0.1 to 30).

When m, n, w, x, y, and z in Formula (6) to Formula (10) are each 0.1 to 30, a lubricant containing the compound is easily applied and a lubricating layer having favorable adhesion is obtained. m, n, w, x, y, and z in Formula (6) to Formula (10) are each preferably 20 or less, more preferably 15 or less, and may be 10 or less. m, n, w, x, y, and z in Formula (6) to Formula (10) are each preferably 1 or more, more preferably 2 or more, and may be 3 or more or 5 or more.

When $R^3$ in Formula (1) is any of Formula (6) to Formula (10), this is preferable because it is easy to synthesize the fluorine-containing ether compound.

When $R^3$ is Formula (6), this is more preferable because the raw material is easily obtained.

In addition, when $R^3$ is any of Formula (6) to Formula (10), the ratio of the number of oxygen atoms (the number of ether bonds (—O—)) to the number of carbon atoms in the perfluoropolyether chain becomes appropriate. Therefore, a fluorine-containing ether compound having an appropriate hardness is obtained. Therefore, the fluorine-containing ether compound applied onto the protective layer is less likely to aggregate on the protective layer, and a thinner lubricating layer can be formed with sufficient coverage. In addition, when $R^3$ is any of Formula (6) to Formula (10), a fluorine-containing ether compound which can form a lubricating layer having favorable wear resistance is obtained.

In the fluorine-containing ether compound represented by Formula (1) according to the present embodiment, at least one of $R^1$—$R^2$— and —$R^4$—$R^5$ has one or more cyano groups. That is, in the fluorine-containing ether compound represented by Formula (1), at least one selected from among $R^1$, $R^2$, $R^4$, and $R^5$ has one or more cyano groups. In the fluorine-containing ether compound of the present embodiment, since at least one of $R^1$—$R^2$— and —$R^4$—$R^5$ has one or more cyano groups, it is possible to form a lubricating layer with favorable adhesion to the protective layer.

The fluorine-containing ether compound represented by Formula (1) may contain two or more cyano groups in the molecule. When the number of cyano groups contained in the molecule is 2 or more, it is preferable that $R^1$—$R^2$— and —$R^4$—$R^5$ each contain one or more cyano groups. When $R^1$—$R^2$— and —$R^4$—$R^5$ each contain one or more cyano groups, in the lubricating layer containing the fluorine-containing ether compound, the adhesion between the lubricating layer and the protective layer becomes better.

In the fluorine-containing ether compound represented by Formula (1), the number of cyano groups contained in the molecule is preferably 3 or less and more preferably 2 or less. When the total number of cyano groups contained in the molecule is 3 or less, this is preferable because it is possible to prevent the occurrence of pickup in which the polarity of the fluorine-containing ether compound becomes too high and the compound adheres as foreign matter (smear) to a magnetic head.

In the fluorine-containing ether compound represented by Formula (1), at least one of $R^2$ and $R^4$ contains one or more secondary amine structures (—NH—). In the fluorine-containing ether compound represented by Formula (1), since a lubricating layer with better adhesion to the protective layer is obtained, the number of secondary amine structures contained in the molecule is preferably 2 or more. When the number of secondary amine structures contained in the molecule is 2 or more, it is preferable that $R^2$ and $R^4$ each contain one or more secondary amine structures. When $R^2$ and $R^4$ each contain one or more secondary amine structures, in the lubricating layer containing the fluorine-containing ether compound, the adhesion between the lubricating layer and the protective layer becomes better.

In the fluorine-containing ether compound represented by Formula (1), the number of secondary amine structures contained in the molecule is preferably 6 or less and more preferably 4 or less. When the number of secondary amine structures contained in the molecule is 6 or less, this is preferable because it is possible to prevent the occurrence of pickup in which the polarity of the fluorine-containing ether compound becomes too high and the compound adheres as foreign matter (smear) to a magnetic head.

In the fluorine-containing ether compound of the present embodiment, the number of hydroxyl groups contained in the molecule is preferably 1 or more and may be 2 or more. When the molecule contains a hydroxyl group, a fluorine-containing ether compound which can form a lubricating layer with better adhesion to the protective layer is obtained. When the number of hydroxyl groups contained in the molecule is 2 or more, it is more preferable that $R^1-R^2-$ and $-R^4-R^5$ each contain one or more hydroxyl groups. When $R^1-R^2-$ and $-R^4-R^5$ each contain one or more hydroxyl groups, in the lubricating layer containing the fluorine-containing ether compound, the adhesion between the lubricating layer and the protective layer becomes better.

In the fluorine-containing ether compound represented by Formula (1), the number of hydroxyl groups contained in the molecule is preferably 3 or less and more preferably 2 or less. When the total number of hydroxyl groups contained in the molecule is 3 or less, the fluorine-containing ether compound is less likely to aggregate on the protective layer due to an intramolecular interaction of the hydroxyl groups. Therefore, a thin lubricating layer can be formed with a better coverage, and better wear resistance is obtained.

In the fluorine-containing ether compound represented by Formula (1), the total number of hydroxyl groups, secondary amine structures (—NH—) and cyano groups contained in the molecule is preferably 8 or less and more preferably 6 or less. In this case, it is possible to prevent the polarity of the fluorine-containing ether compound from becoming too high and to prevent pickup from occurring.

In the fluorine-containing ether compound represented by Formula (1), preferably, the number of secondary amine structures contained in the molecule is 2 or more, the number of hydroxyl groups is 3 or less, the number of cyano groups is 3 or less, and the total number of secondary amine structures, hydroxyl groups and cyano groups is 8 or less. In this case, the fluorine-containing ether compound is less likely to aggregate on the protective layer due to an intramolecular interaction of the hydroxyl groups and a synergistic effect of strong interaction with the protective layer due to the inclusion of the secondary amine structure and the cyano group is obtained. As a result, a fluorine-containing ether compound which can form a lubricating layer having better wear resistance and spin-off resistance is obtained.

In the fluorine-containing ether compound represented by Formula (1), $R^1$ and $R^5$ may be the same as or different from each other. When $R^1$ and $R^5$ are the same, a fluorine-containing ether compound, which easily wets and spreads uniformly on the protective layer and from which a lubricating layer having a uniform film thickness is easily obtained, is obtained. As a result, the lubricating layer containing the fluorine-containing ether compound tends to have a favorable coverage, and even better wear resistance is obtained. In addition, when $R^1$ and $R^5$ are the same, the fluorine-containing ether compound can be easily produced.

In addition, in the fluorine-containing ether compound represented by Formula (1), $R^2$ and $R^4$ may be the same as or different from each other. When $R^2$ and $R^4$ are the same, a fluorine-containing ether compound, which easily wets and spreads uniformly on the protective layer and from which a lubricating layer having a uniform film thickness is easily obtained, is obtained. When $R^2$ and $R^4$ are the same, the fluorine-containing ether compound tends to be easily produced.

In addition, in the fluorine-containing ether compound represented by Formula (1), when $R^1$ and $R^5$ are the same and $R^2$ and $R^4$ are the same, the compound can be easily produced. In addition, when $R^1$ and $R^5$ are the same and $R^2$ and $R^4$ are the same, a fluorine-containing ether compound, which easily wets and spreads uniformly on the protective layer and from which a lubricating layer having a more uniform film thickness is easily obtained, is obtained.

Specifically, the fluorine-containing ether compound represented by Formula (1) is preferably any of the compounds represented by the following Formulae (A) to (Z). Here, in Formulae (A) to (Z), since the average degrees of polymerization (repeating numbers) ma to my, na to nv, w, x, y, and z are values indicating average values, they are not necessarily integers.

In the compound represented by Formula (A), in Formula (1), $R^1$ is a 3-cyanopropyl group, $R^2$ has [A], and $R^3$ is Formula (6). In the compound represented by Formula (A), $R^1$ and $R^5$ are the same, and $R^2$ and $R^4$ are the same.

In the compound represented by Formula (B), in Formula (1), $R^1$ is a 4-cyanobutyl group, $R^2$ has [A], and $R^3$ is Formula (6). In the compound represented by Formula (B), $R^1$ and $R^5$ are the same and $R^2$ and $R^4$ are the same.

In the compound represented by Formula (C), in Formula (1), $R^1$ is a 2-cyanopropyl group, $R^2$ has [A], and $R^3$ is Formula (6). In the compound represented by Formula (C), $R^1$ and $R^5$ are the same and $R^2$ and $R^4$ are the same.

In the compound represented by Formula (D), in Formula (1), $R^1$ is a 3-cyanopropyl group, $R^2$ has two [A]'s, and $R^3$ is Formula (6). In the compound represented by Formula (D), $R^1$ and $R^5$ are the same and $R^2$ and $R^4$ are the same.

In the compound represented by Formula (E), in Formula (1), $R^1$ is a 3-cyanopropyl group, $R^2$ has two [A]'s, and $R^3$ is Formula (6). In the compound represented by Formula (E), $R^1$ and $R^5$ are the same and $R^2$ and $R^4$ are the same.

In the compound represented by Formula (F), in Formula (1), $R^1$ is a 3-cyanopropyl group, $R^2$ has [A] and [B], and $R^3$ is Formula (6). In the compound represented by Formula (F), $R^1$ and $R^5$ are the same and $R^2$ and $R^4$ are the same.

In the compound represented by Formula (G), in Formula (1), $R^1$ is a 3-hydroxypropyl group, $R^2$ has [A] and [B], and $R^3$ is Formula (6). In the compound represented by Formula (G), $R^1$ and $R^5$ are the same and $R^2$ and $R^4$ are the same.

In the compound represented by Formula (H), in Formula (1), $R^1$ is a 2-hydroxyethyl group, $R^2$ has [A], and $R^3$ is Formula (6). $R^4$ has [C], and $R^5$ is a 3-cyanopropyl group.

In the compound represented by Formula (I), in Formula (1), $R^1$ is a 3-hydroxypropyl group, $R^2$ has two [A]'s, and $R^3$ is Formula (6). $R^4$ has [C], and $R^5$ is a 3-cyanopropyl group.

In the compound represented by Formula (J), in Formula (1), $R^1$ is a 3-cyanopropyl group, $R^2$ has [A], and $R^3$ is Formula (6). $R^4$ has [C], and $R^5$ is the same as $R^1$.

In the compound represented by Formula (K), in Formula (1), $R^1$ is a 4-hydroxybutyl group, $R^2$ has [A] and [B], and $R^3$ is Formula (6). $R^4$ has [C], and $R^5$ is a 3-cyanopropyl group.

In the compound represented by Formula (L), in Formula (1), $R^1$ is a 3-cyanopropyl group, $R^2$ has [A] and [B], and $R^3$ is Formula (6). $R^4$ has [C], and $R^5$ is the same as $R^1$.

In the compound represented by Formula (M), in Formula (1), $R^1$ is a 2-propynyl group, $R^2$ has [A], and $R^3$ is Formula (6). $R^4$ has [C], and $R^5$ is a 3-cyanopropyl group.

In the compound represented by Formula (N), $R^1$ is a propyl group, $R^2$ has [A], and $R^3$ is Formula (6). $R^4$ has [C], and $R^5$ is a 3-cyanopropyl group.

In the compound represented by Formula (O), in Formula (1), $R^1$ is a 4-methoxyphenyl group, $R^2$ has [A], and $R^3$ is Formula (6). $R^4$ has [C], and $R^5$ is a 3-cyanopropyl group.

In the compound represented by Formula (P), in Formula (1), $R^1$ is an allyl group, $R^2$ has two [A]'s, and $R^3$ is Formula (6). $R^4$ has [C], and $R^5$ is a 3-cyanopropyl group.

In the compound represented by Formula (Q), in Formula (1), $R^1$ is a 3-butenyl group, $R^2$ has [A] and [B], and $R^3$ is Formula (6). $R^4$ has [C], and $R^5$ is a 3-cyanopropyl group.

In the compound represented by Formula (R), in Formula (1), $R^1$ is a 3-cyanopropyl group, $R^2$ has three [A]'s, and $R^3$ is Formula (6). $R^4$ has [C], and $R^5$ is the same as $R^1$.

In the compound represented by Formula (S), in Formula (1), $R^1$ is a 2-hydroxyethyl group, $R^2$ has one [A] and two [B]'s, and $R^3$ is Formula (6). $R^4$ has [C], and $R^5$ is a 3-cyanopropyl group.

In the compound represented by Formula (T), in Formula (1), $R^1$ is a 3-cyanopropyl group, $R^2$ has two [A]'s and one [B], and $R^3$ is Formula (6). $R^4$ has [C], and $R^5$ is the same as $R^1$.

In the compound represented by Formula (U), in Formula (1), $R^1$ is an allyl group, $R^2$ has [A], and $R^3$ is Formula (6). $R^4$ has [C], and $R^5$ is a 4-cyano-2-(cyanomethyl)butyl group.

In the compound represented by Formula (V), in Formula (1), $R^1$ is an allyl group, $R^2$ has three [A]'s, and $R^3$ is Formula (6). $R^4$ has [C], and $R^5$ is a 4-cyano-2-(cyanomethyl)butyl group.

In the compound represented by Formula (W), in Formula (1), $R^1$ is an allyl group, $R^2$ has two [A]'s, and $R^3$ is Formula (7). $R^4$ has [C], and $R^5$ is a 3-cyanopropyl group.

In the compound represented by Formula (X), in Formula (1), $R^1$ is an allyl group, $R^2$ has two [A]'s, and $R^3$ is Formula (8). $R^4$ has [C], and $R^5$ is a 3-cyanopropyl group.

In the compound represented by Formula (Y), in Formula (1), $R^1$ is an allyl group, $R^2$ has two [A]'s, and $R^3$ is Formula (9). $R^4$ has [C], and $R^5$ is a 3-cyanopropyl group.

In the compound represented by Formula (Z), in Formula (1), $R^1$ is an allyl group, $R^2$ has two [A]'s, and $R^3$ is Formula (10). $R^4$ has [C], and $R^5$ is a 3-cyanopropyl group.

The compounds represented by Formulae (A) to (Z) are shown below.

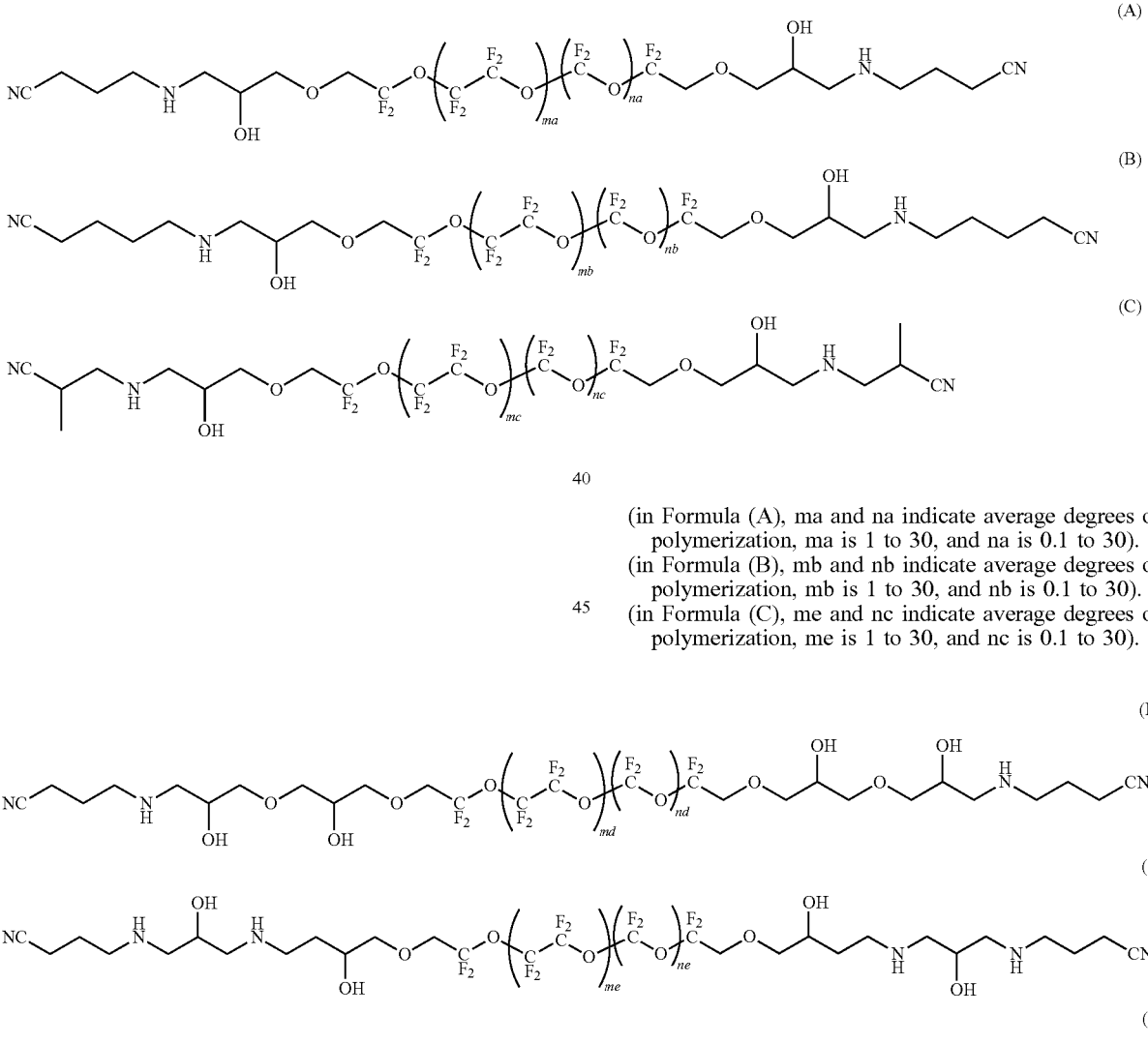

(in Formula (A), ma and na indicate average degrees of polymerization, ma is 1 to 30, and na is 0.1 to 30).
(in Formula (B), mb and nb indicate average degrees of polymerization, mb is 1 to 30, and nb is 0.1 to 30).
(in Formula (C), me and nc indicate average degrees of polymerization, me is 1 to 30, and nc is 0.1 to 30).

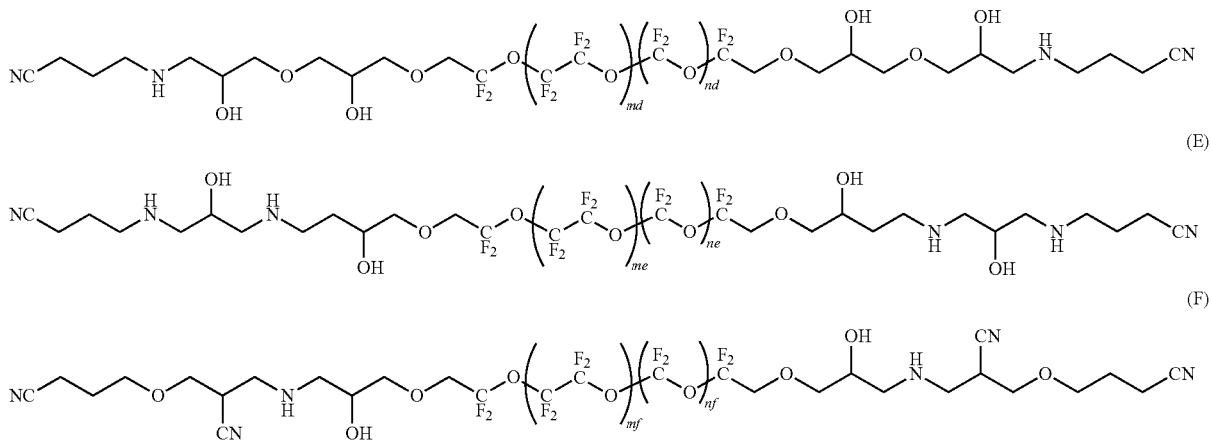

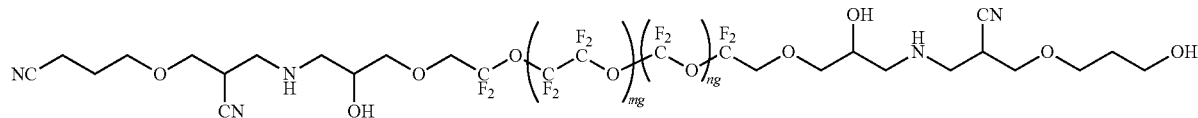

(in Formula (D), md and nd indicate average degrees of polymerization, and md is 1 to 30, nd is 0.1 to 30).
(in Formula (E), me and ne indicate average degrees of polymerization, and me is 1 to 30, ne is 0.1 to 30).
(in Formula (F), mf and nf indicate average degrees of polymerization, and mf is 1 to 30, nf is 0.1 to 30).
(in Formula (G), mg and ng indicate average degrees of polymerization, and mg is 1 to 30, ng is 0.1 to 30).

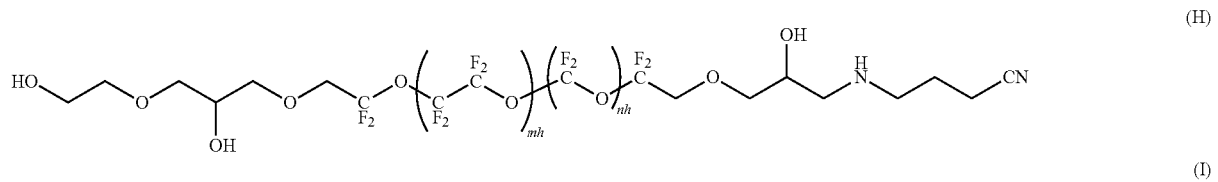

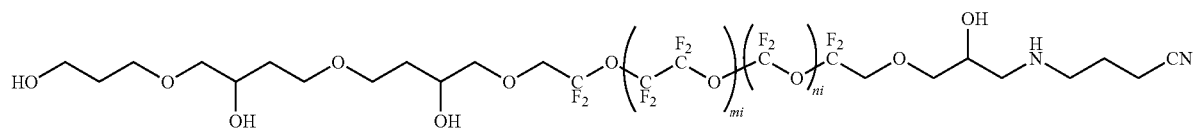

(in Formula (H), mh and nh indicate average degrees of polymerization, mh is 1 to 30, and nh is 0.1 to 30).
(in Formula (I), mi and ni indicate average degrees of polymerization, mi is 1 to 30, and ni is 0.1 to 30).

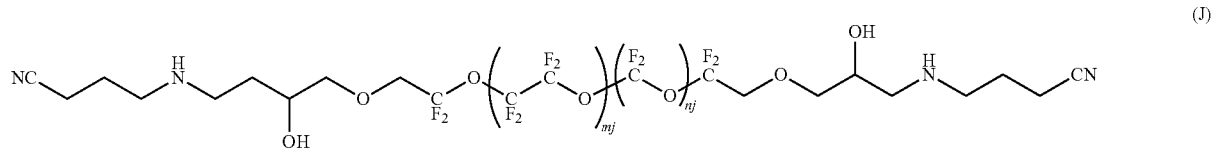

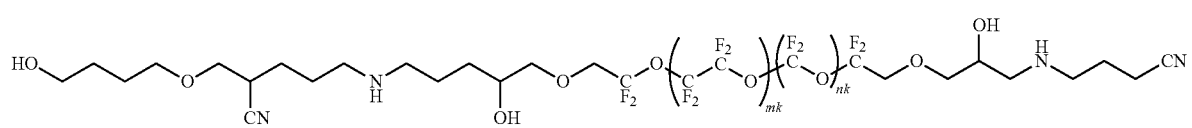

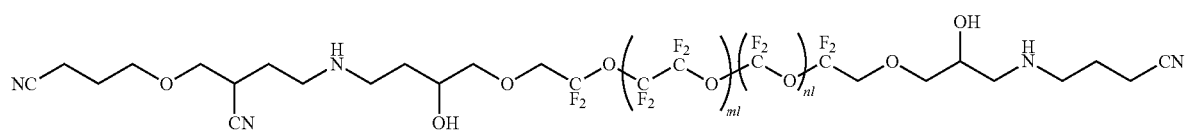

(in Formula (J), mj and nj indicate average degrees of polymerization, mj is 1 to 30, and nj is 0.1 to 30).
(in Formula (K), mk and nk indicate average degrees of polymerization, mk is 1 to 30, and nk is 0.1 to 30).
(in Formula (L), ml and nl indicate average degrees of polymerization, ml is 1 to 30, and nl is 0.1 to 30).

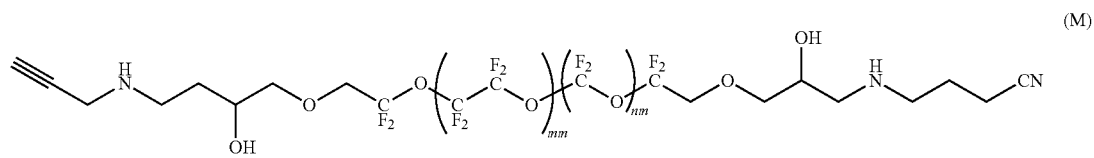

(M)

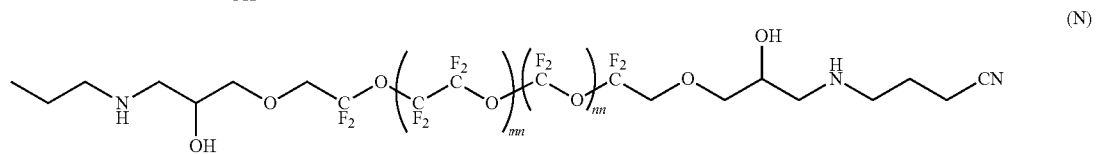

(N)

(in Formula (M), mm and nm indicate average degrees of polymerization, mm is 1 to 30, and nm is 0.1 to 30).

(in Formula (N), mn and nn indicate average degrees of polymerization, mn is 1 to 30, and nn is 0.1 to 30).

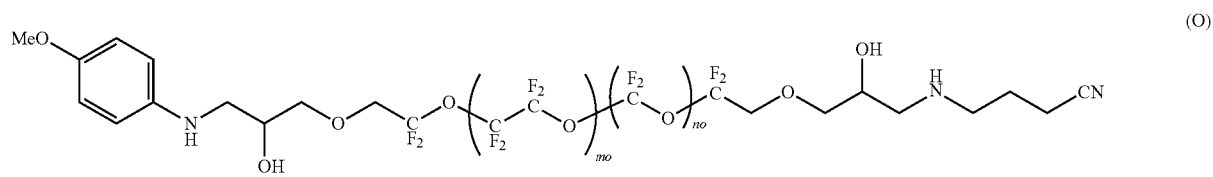

(O)

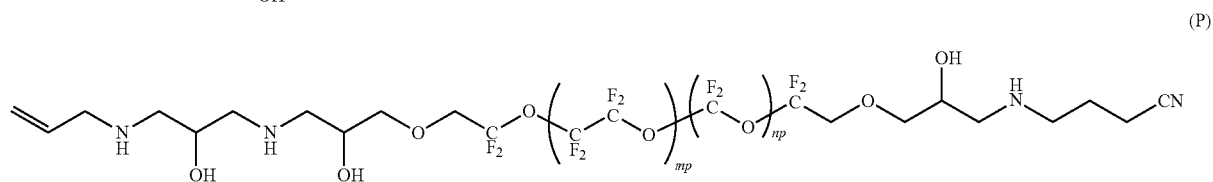

(P)

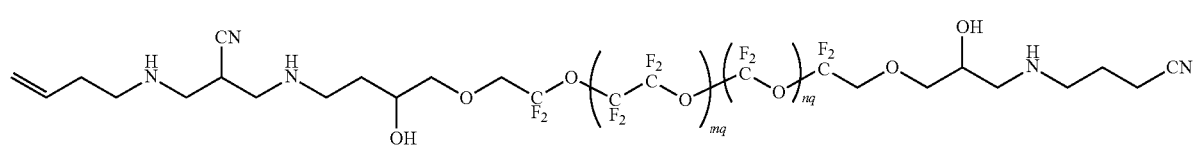

(Q)

(in Formula (O), mo and no indicate average degrees of polymerization, mo is 1 to 30, and no is 0.1 to 30).
(in Formula (P), mp and np indicate average degrees of polymerization, mp is 1 to 30, and np is 0.1 to 30).
(in Formula (Q), mq and nq indicate average degrees of polymerization, mq is 1 to 30, and nq is 0.1 to 30).

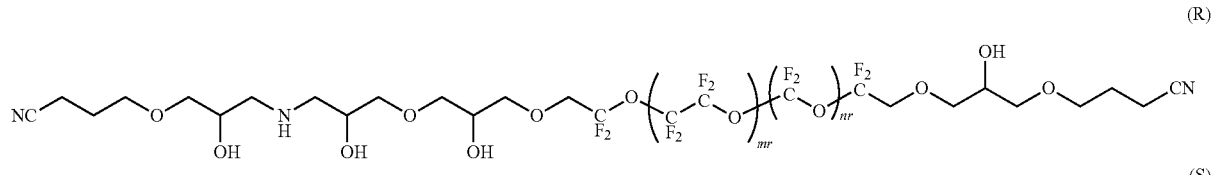

(R)

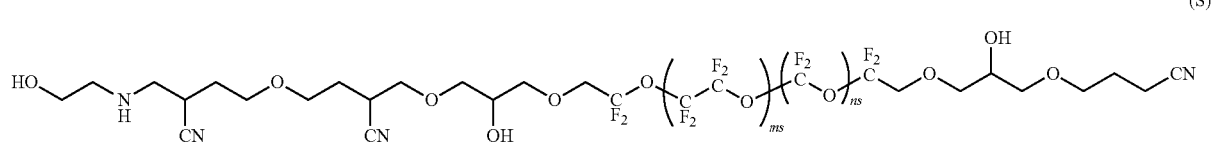

(S)

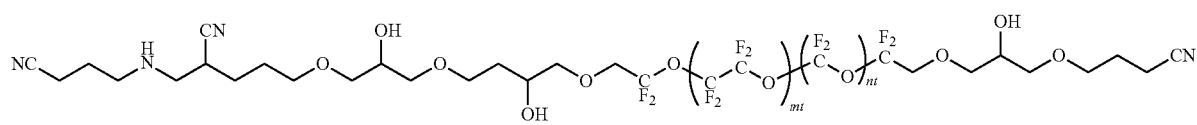

(T)

(in Formula (R), mr and nr indicate average degrees of polymerization, mr is 1 to 30, and nr is 0.1 to 30).
(in Formula (S), ms and ns indicate average degrees of polymerization, ms is 1 to 30, and ns is 0.1 to 30).
(in Formula (T), mt and nt indicate average degrees of polymerization, mt is 1 to 30, and nt is 0.1 to 30).

When the compound represented by Formula (1) is any of the compounds represented by Formulae (A) to (Z), this is preferable because a raw material is easily available and it is possible to form a lubricating layer having excellent wear resistance and spin-off resistance even if the thickness is thin. Among these, any of the compounds represented by

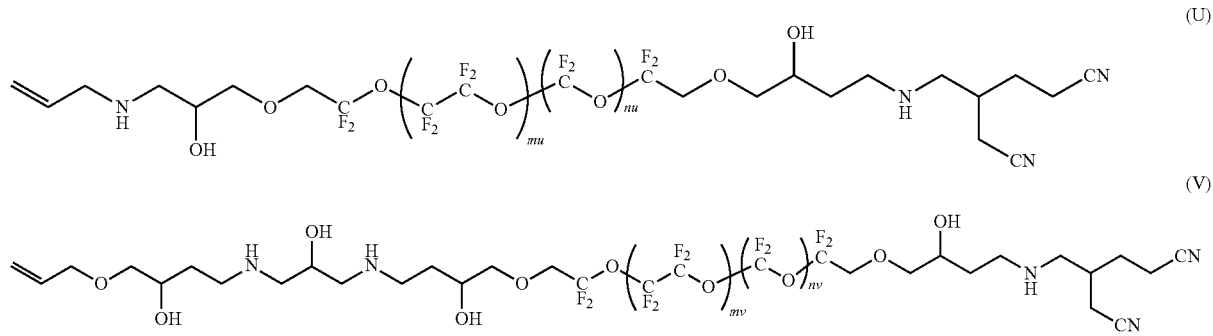

(in Formula (U), mu and nu indicate average degrees of polymerization, mu is 1 to 30, and nu is 0.1 to 30).
(in Formula (V), mv and nv indicate average degrees of polymerization, mv is 1 to 30, and nv is 0.1 to 30).

Formulae (A) to (C), (J) to (Q), (U), and (W) to (Z) is more preferable because it is possible to form a lubricating layer having better wear resistance. Particularly, any of the compounds represented by Formulae (A), (J), (P), (Q) and (U) is

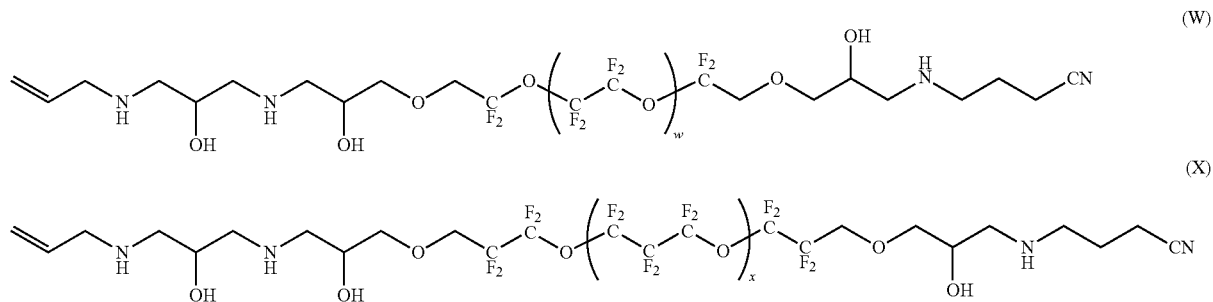

(in Formula (W), w indicates the average degree of polymerization, and w is 0.1 to 30).
(in Formula (X), x indicates the average degree of polymerization, and x is 0.1 to 30).

preferable. This is because, when secondary amine structures are disposed in appropriate numbers and appropriate positions for $R^2$ and $R^4$, and cyano groups are disposed in appropriate numbers and appropriate positions for at least

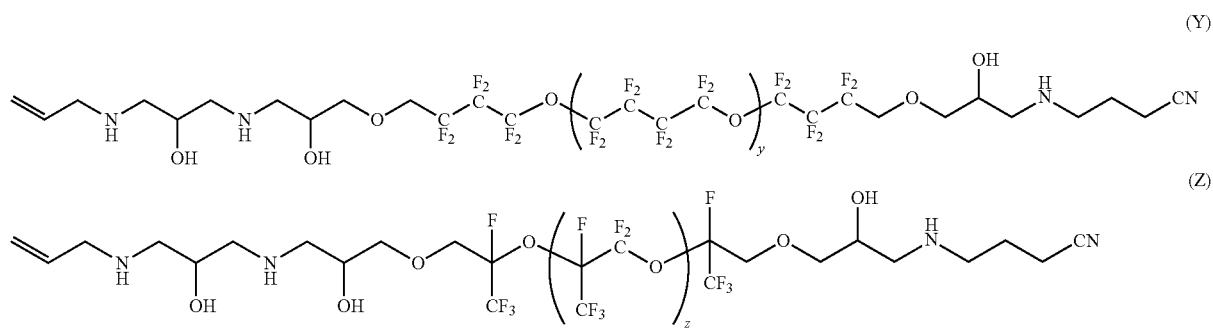

(in Formula (Y), y indicates the average degree of polymerization, and y is 0.1 to 30).
(in Formula (Z), z indicates the average degree of polymerization, and z is 0.1 to 30).

one of $R^1$—$R^2$— and —$R^4$—$R^5$, the adhesion between the lubricating layer and the protective layer becomes better.

The number-average molecular weight (Mn) of the fluorine-containing ether compound of the present embodiment is preferably in a range of 500 to 10,000. When the number-average molecular weight is 500 or more, the lubricant containing the fluorine-containing ether compound of the present embodiment is less likely to evaporate, and a lubricating layer in which a decrease in film thickness due to spin-off is less likely to occur can be formed. In addition, when the number-average molecular weight is 500 or more, it is possible to prevent the lubricant from evaporating and transferring to a magnetic head. The number-average molecular weight of the fluorine-containing ether compound is more preferably 1,000 or more. In addition, when the number-average molecular weight is 10,000 or less, the viscosity of the fluorine-containing ether compound is appropriate, and when a lubricant containing the compound is applied, a thin lubricating layer can be easily formed. The number-average molecular weight of the fluorine-containing ether compound is more preferably 3,000 or less so that the compound has a viscosity at which handling is easy when applied to a lubricant.

The number-average molecular weight (Mn) of the fluorine-containing ether compound is a value measured through $^1$H-NMR and $^{19}$F-NMR using AVANCE III 400 (commercially available from Bruker BioSpin). In the measurement of nuclear magnetic resonance (NMR), a sample is diluted with a single solvent such as hexafluorobenzene, d-acetone, and d-tetrahydrofuran or a mixed solvent, and used for measurement. The standard for $^{19}$F-NMR chemical shift is −164.7 ppm for the peak of hexafluorobenzene, and the standard for $^1$H-NMR chemical shift is 2.2 ppm for the peak of acetone.

"Production Method"

A method of producing a fluorine-containing ether compound of the present embodiment is not particularly limited, and a conventionally known production method can be used for production. The fluorine-containing ether compound of the present embodiment can be produced using, for example, the following production method.

First, a fluorine-based compound in which a hydroxymethyl group (—CH$_2$OH) is disposed at both terminals of the perfluoropolyether chain corresponding to R$^3$ in Formula (1) is prepared.

Next, the hydroxyl group of the hydroxymethyl group disposed at one terminal of the fluorine-based compound is substituted with a group composed of R$^1$—R$^2$— in Formula (1) (first reaction). Then, the hydroxyl group of the hydroxymethyl group disposed at the other terminal is substituted with the terminal group composed of —R$^4$—R$^5$ in Formula (1) (second reaction).

The first reaction and the second reaction can be performed using a conventionally known method, and can be appropriately determined according to the types of R$^1$, R$^2$, R$^4$, and R$^5$ and the like in Formula (1). In addition, either the first reaction or the second reaction may be performed first. When R$^1$ and R$^5$ are the same, and R$^2$ and R$^4$ are the same, the first reaction and the second reaction may be performed at the same time.

According to the above method, a compound represented by Formula (1) is obtained.

In the present embodiment, in order to produce a fluorine-containing ether compound in which —R$^2$—O— is represented by Formula (2) and —O—R$^4$— is represented by Formula (3), it is preferable to use an epoxy compound. For the epoxy compound, a commercial product may be purchased or the compound may be synthesized. When the epoxy compound is synthesized, it can be synthesized using, for example, the following (a) and (b). The epoxy compound may be synthesized by a method of oxidizing an unsaturated bond.

(a) An alcohol or a protected amine having a structure corresponding to the terminal group represented by R$^1$ or R$^5$ of the fluorine-containing ether compound to be produced.

(b) Any one selected from among epichlorohydrin, epibromohydrin, and 2-bromoethyloxirane.

The fluorine-containing ether compound of the present embodiment is the compound represented by Formula (1). Therefore, when a lubricating layer is formed on the protective layer using the lubricant containing the compound, in Formula (1), the PFPE chain represented by R$^3$ covers the surface of the protective layer and reduces the frictional force between the magnetic head and the protective layer.

In addition, in the lubricating layer formed using the lubricant containing the fluorine-containing ether compound of the present embodiment, the fluorine-containing ether compound is less likely to aggregate on the protective layer due to an intramolecular interaction between the terminal groups represented by R$^1$ and R$^5$ in Formula (1), the secondary amine structure (—NH—) contained in at least one of R$^2$ and R$^4$, and the cyano group contained in at least one of R$^1$—R$^2$— and —R$^4$—R$^5$. Moreover, a strong interaction with the protective layer is obtained according to a synergistic effect obtained by the inclusion of the secondary amine structure and the cyano group. Accordingly, it is possible to form a lubricating layer having excellent wear resistance and spin-off resistance using the fluorine-containing ether compound of the present embodiment.

[Lubricant for Magnetic Recording Medium]

A lubricant for a magnetic recording medium of the present embodiment contains a fluorine-containing ether compound represented by Formula (1).

The lubricant of the present embodiment can be used by being mixed with a known material used as a material for lubricants as necessary, as long as the characteristics thereof which are obtained due to the inclusion of the fluorine-containing ether compound represented by Formula (1) are not impaired.

Specific examples of known materials include, for example, FOMBLIN (registered trademark) ZDIAC, FOMBLIN ZDEAL, and FOMBLIN AM-2001 (all commercially available from Solvay Solexis), and Moresco A20H (commercially available from Moresco). A known material used in combination with the lubricant of the present embodiment preferably has a number-average molecular weight of 1,000 to 10,000.

When lubricant of the present embodiment contains a material other than the fluorine-containing ether compound represented by Formula (1), the content of the fluorine-containing ether compound represented by Formula (1) in the lubricant of the present embodiment is preferably 50 mass % or more, and more preferably 70 mass % or more. The upper limit can be arbitrarily selected, and may be, for example, 99 mass % or less, 95 mass % or less, 90 mass % or less, or 85 mass % or less.

Since the lubricant of the present embodiment contains the fluorine-containing ether compound represented by Formula (1), it is possible to form a lubricating layer which can cover the surface of the protective layer with a high coverage even if the thickness is thin and which has excellent adhesion to the protective layer. Therefore, according to the lubricant of the present embodiment, it is possible to form a lubricating layer which has excellent wear resistance even if the thickness is thin and in which a decrease in film thickness due to spin-off is less likely to occur.

In addition, since the lubricant of the present embodiment contains the fluorine-containing ether compound represented by Formula (1), the fluorine-containing ether compound in the lubricating layer that is present without adhering (adsorbing) to the protective layer is less likely to aggregate. Therefore, it is possible to prevent the fluorine-containing ether compound from aggregating and adhering as foreign matter (smear) to a magnetic head, and reduce the occurrence of pickup.

In addition, since the lubricant of the present embodiment contains the fluorine-containing ether compound represented by Formula (1), it is possible to form a lubricating layer having excellent wear resistance and spin-off resistance due to an interaction between the terminal groups represented by $R^1$ and $R^5$, the secondary amine structure (—NH—) contained in at least one of $R^2$ and $R^4$, the cyano group contained in at least one of $R^1$—$R^2$— and —$R^4$—$R^5$ in Formula (1), and the protective layer.

[Magnetic Recording Medium]

In a magnetic recording medium of the present embodiment, at least a magnetic layer, a protective layer, and a lubricating layer are sequentially provided on a substrate.

In the magnetic recording medium of the present embodiment, as necessary, one, two or more underlayers can be provided between the substrate and the magnetic layer. In addition, an adhesive layer and/or a soft magnetic layer can be provided between the underlayer and the substrate.

The FIGURE is a schematic cross-sectional view showing a magnetic recording medium according to one embodiment of the present invention.

A magnetic recording medium 10 of the present embodiment has a structure in which an adhesive layer 12, a soft magnetic layer 13, a first underlayer 14, a second underlayer 15, a magnetic layer 16, a protective layer 17, and a lubricating layer 18 are sequentially provided on a substrate 11.

"Substrate"

The substrate 11 can be arbitrarily selected. As the base material 11, for example, a non-magnetic substrate or the like in which a film made of NiP or a NiP alloy is formed on a base made of a metal or an alloy material such as Al or an Al alloy can be preferably used.

In addition, as the substrate 11, a non-magnetic substrate made of a non-metal material such as glass, a ceramic, silicon, silicon carbide, carbon, and a resin may be used, or a non-magnetic substrate in which a film of NiP or a NiP alloy is additionally formed on a base made of the non-metal material may be used as the substrate 11.

"Adhesive Layer"

The adhesive layer 12 prevents the progress of corrosion of the substrate 11 that occurs when the substrate 11 and the soft magnetic layer 13 which is provided on the adhesive layer 12 are disposed in contact with each other.

The material of the adhesive layer 12 can be arbitrarily selected, and can be appropriately selected from among, for example, Cr, a Cr alloy, Ti, a Ti alloy, CrTi, NiAl, and an AlRu alloy. The adhesive layer 12 can be formed by, for example, a sputtering method.

"Soft Magnetic Layer"

The soft magnetic layer 13 can be arbitrarily selected, and preferably has a structure in which a first soft magnetic film, an intermediate layer made of a Ru film, and a second soft magnetic film are sequentially laminated. That is, the soft magnetic layer 13 preferably has a structure in which an intermediate layer made of a Ru film is interposed between two soft magnetic film layers, and thus the soft magnetic films above and below the intermediate layer are bonded by anti-ferromagnetic coupling (AFC).

Examples of materials of the first soft magnetic film and the second soft magnetic film include a CoZrTa alloy and a CoFe alloy.

It is preferable to add any of Zr, Ta, and Nb to the CoFe alloy used for the first soft magnetic film and the second soft magnetic film. Thereby, the amorphization of the first soft magnetic film and the second soft magnetic film can be promoted, the orientation of the first underlayer (seed layer) can be improved, and the floating height of the magnetic head can be reduced.

The soft magnetic layer 13 can be formed by, for example, a sputtering method.

"First Underlayer"

The first underlayer 14 is a layer that controls the orientation and the crystal size of the second underlayer 15 and the magnetic layer 16 provided thereon.

Examples of the first underlayer 14 include a Cr layer, a Ta layer, a Ru layer, and a CrMo alloy layer, a CoW alloy layer, a CrW alloy layer, a CrV alloy layer, and a CrTi alloy layer.

The first underlayer 14 can be formed by, for example, a sputtering method.

"Second Underlayer"

The second underlayer 15 is a layer that controls the orientation of the magnetic layer 16 such that it becomes favorable. The second underlayer 15 can be arbitrarily selected, but it is preferably a layer made of Ru or a Ru alloy.

The second underlayer 15 may be single layer or may be composed of a plurality of layers. When the second underlayer 15 is composed of a plurality of layers, all of the layers may be composed of the same material, or at least one layer may be composed of a different material.

The second underlayer 15 can be formed by, for example, a sputtering method.

"Magnetic Layer"

The magnetic layer 16 is made of a magnetic film in which the axis of easy magnetization is in a direction perpendicular or horizontal to the surface of the substrate. The magnetic layer 16 can be arbitrarily selected, and is preferably a layer containing Co and Pt, and may be a layer containing an oxide, Cr, B, Cu, Ta, Zr or the like in order to further improve SNR characteristics.

Examples of oxides contained in the magnetic layer 16 include $SiO_2$, SiO, $Cr_2O_3$, CoO, $Ta_2O_3$, and $TiO_2$.

The magnetic layer 16 may be composed of a single layer or may be composed of a plurality of magnetic layers made of materials with different compositions.

For example, when the magnetic layer 16 is composed of three layers including a first magnetic layer, a second magnetic layer, and a third magnetic layer sequentially laminated from below, the first magnetic layer preferably has a granular structure made of a material containing Co, Cr, and Pt, and further containing an oxide. As the oxide contained in the first magnetic layer, for example, it is preferable to use an oxide of Cr, Si, Ta, Al, Ti, Mg, Co or the like. Among these, particularly, $TiO_2$, $Cr_2O_3$, $SiO_2$ or the like can be preferably used. In addition, the first magnetic layer is preferably made of a composite oxide in which two or more oxides are added. Among these, particularly, $Cr_2O_3$—$SiO_2$, $Cr_2O_3$—$TiO_2$, $SiO_2$—$TiO_2$ or the like can be preferably used.

The first magnetic layer can contain one or more elements selected from the group consisting of B, Ta, Mo, Cu, Nd, W, Nb, Sm, Tb, Ru, and Re in addition to Co, Cr, Pt, and an oxide.

For the second magnetic layer, the same material as for the first magnetic layer can be used. The second magnetic layer preferably has a granular structure.

The third magnetic layer preferably has a non-granular structure made of a material containing Co, Cr, and Pt, and not containing an oxide. The third magnetic layer can contain one or more elements selected from the group consisting of B, Ta, Mo, Cu, Nd, W, Nb, Sm, Tb, Ru, Re, and Mn in addition to Co, Cr, and Pt.

When the magnetic layer 16 is formed of a plurality of magnetic layers, it is preferable to provide a non-magnetic layer between adjacent magnetic layers. When the magnetic layer 16 is composed of three layers including a first magnetic layer, a second magnetic layer, and a third magnetic layer, it is preferable to provide a non-magnetic layer between the first magnetic layer and the second magnetic layer, and between the second magnetic layer and the third magnetic layer.

For the non-magnetic layer provided between adjacent magnetic layers of the magnetic layer 16, for example, Ru, a Ru alloy, a CoCr alloy, a CoCrX1 alloy (X1 represents one, two or more elements selected from among Pt, Ta, Zr, Re, Ru, Cu, Nb, Ni, Mn, Ge, Si, O, N, W, Mo, Ti, V, and B), or the like can be preferably used.

For the non-magnetic layer provided between adjacent magnetic layers of the magnetic layer 16, it is preferable to use an alloy material containing an oxide, a metal nitride, or a metal carbide. Specifically, as the oxide, for example, $SiO_2$, $Al_2O_3$, $Ta_2O_5$, $Cr_2O_3$, MgO, $Y_2O_3$, $TiO_2$ or the like can be used. As the metal nitride, for example, AlN, $Si_3N_4$, TaN, CrN or the like can be used. As the metal carbide, for example, TaC, BC, SiC or the like can be used.

The non-magnetic layer can be formed by, for example, a sputtering method.

The magnetic layer 16 is preferably a magnetic layer for perpendicular magnetic recording in which the axis of easy magnetization is in a direction perpendicular to the surface of the substrate in order to realize a higher recording density. The magnetic layer 16 may be a magnetic layer for in-plane magnetic recording.

The magnetic layer 16 may be formed by any conventionally known method such as a deposition method, an ion beam sputtering method, and a magnetron sputtering method. The magnetic layer 16 is generally formed by a sputtering method.

"Protective Layer"

The protective layer 17 protects the magnetic layer 16. The protective layer 17 may be composed of one layer or may be composed of a plurality of layers. Examples of materials of the protective layer 17 include carbon, carbon containing nitrogen, and silicon carbide.

As the protective layer 17, a carbon-based protective layer can be preferably used, and an amorphous carbon protective layer is particularly preferable. When the protective layer 17 is a carbon-based protective layer, this is preferable because the interaction with the polar group (particularly the hydroxyl group) contained in the fluorine-containing ether compound in the lubricating layer 18 is further improved.

The adhesive force between the carbon-based protective layer and the lubricating layer 18 can be controlled by forming the carbon-based protective layer with hydrogenated carbon and/or nitrogenized carbon and adjusting the hydrogen content and/or the nitrogen content in the carbon-based protective layer. The hydrogen content in the carbon-based protective layer measured by a hydrogen forward scattering method (HFS) is preferably 3 to 20 atom %. In addition, the nitrogen content in the carbon-based protective layer measured through X-ray photoelectron spectroscopy (XPS) is preferably 4 to 15 atom %.

Hydrogen and/or nitrogen contained in the carbon-based protective layer need not be uniformly contained throughout the entire carbon-based protective layer. For example, the carbon-based protective layer is preferably formed as a composition gradient layer in which nitrogen is contained in the protective layer 17 on the side of the lubricating layer 18 and hydrogen is contained in the protective layer 17 on the side of the magnetic layer 16. In this case, the adhesive force between the carbon-based protective layer and the magnetic layer 16 and the lubricating layer 18 is further improved.

The film thickness of the protective layer 17 may be 1 nm to 7 nm. When the film thickness of the protective layer 17 is 1 nm or more, the performance of the protective layer 17 can be sufficiently obtained. The film thickness of the protective layer 17 is preferably 7 nm or less, from the viewpoint of film thinning of the protective layer 17.

As a film forming method for the protective layer 17, a sputtering method using a target material containing carbon, a chemical vapor deposition (CVD) method using a hydrocarbon raw material such as ethylene or toluene, an ion beam deposition (IBD) method or the like can be used.

When a carbon-based protective layer is formed as the protective layer 17, for example, a film can be formed by a DC magnetron sputtering method. In particular, when a carbon-based protective layer is formed as the protective layer 17, it is preferable to form an amorphous carbon protective layer by a plasma CVD method. The amorphous carbon protective layer formed by the plasma CVD method has uniform surfaces and low roughness.

"Lubricating Layer"

The lubricating layer 18 prevents contamination of the magnetic recording medium 10. In addition, the lubricating layer 18 reduces a frictional force of a magnetic head of a magnetic recording/reproducing device, which slides on the magnetic recording medium 10, and improves the durability of the magnetic recording medium 10.

As shown in the FIGURE, the lubricating layer 18 is formed on and in contact with the protective layer 17. The lubricating layer 18 contains the above fluorine-containing ether compound.

When the protective layer 17 disposed below the lubricating layer 18 is a carbon-based protective layer, particularly, the lubricating layer 18 is bonded to the protective layer 17 with a high bonding force. As a result, even if the thickness of the lubricating layer 18 is thin, it is easy to obtain the magnetic recording medium 10 in which the surface of the protective layer 17 is covered with a high coverage, and it is possible to effectively prevent contamination of the surface of the magnetic recording medium 10.

The average film thickness of the lubricating layer 18 can be arbitrarily selected, and is preferably 0.5 nm (5 Å) to 2.0 nm (20 Å), and more preferably 0.5 nm (5 Å) to 1.0 nm (10 Å). When the average film thickness of the lubricating layer 18 is 0.5 nm or more, the lubricating layer 18 is formed with a uniform film thickness without forming an island shape or a mesh shape. Therefore, the lubricating layer 18 covers the surface of the protective layer 17 with a high coverage, and a decrease in film thickness due to spin-off is less likely to occur. In addition, when the average film thickness of the lubricating layer 18 is 2.0 nm or less, the lubricating layer 18 can be sufficiently thinned, and the floating height of the magnetic head can be sufficiently reduced.

When the surface of the protective layer 17 is not sufficiently covered with the lubricating layer 18 with a high coverage, environmental substances adsorbed on the surface of the magnetic recording medium 10 pass through voids of the lubricating layer 18 and enter a layer below the lubricating layer 18. The environmental substances that have entered the layer below the lubricating layer 18 are adsorbed and bonded to the protective layer 17 and produce contamination substances. Thus, during magnetic recording/reproducing, the contamination substances (aggregated components) adhere (transfers) to a magnetic head as a smear, the magnetic head may be damaged, and magnetic recording/reproducing characteristics of the magnetic recording/reproducing device may deteriorate.

Examples of environmental substances that generate contamination substances include siloxane compounds (cyclic siloxanes and linear siloxanes), ionic impurities, hydrocarbon with a relatively high molecular weight such as octacosan, and plasticizers such as dioctyl phthalate. Examples of metal ions contained in ionic impurities include sodium ions and potassium ions. Examples of inorganic ions contained in ionic impurities include chlorine ions, bromide ions, nitrate ions, sulfate ions, and ammonium ions. Examples of organic ions contained in ionic impurities include oxalate ions and formate ions.

"Method of Forming Lubricating Layer"

Examples of a method of forming the lubricating layer 18 include a method in which a magnetic recording medium is prepared during production in which respective layers up to the protective layer 17 are formed on the substrate 11, and a solution for forming a lubricating layer is applied onto the protective layer 17 and dried.

The solution for forming a lubricating layer can be obtained by dispersing and dissolving the lubricant for a magnetic recording medium of the embodiment described above in a solvent as necessary, and adjusting the viscosity and concentration to be suitable for application methods.

Examples of solvents used for the solution for forming a lubricating layer include fluorine-based solvents such as Vertrel (registered trademark) XF (product name, commercially available from Du Pont-Mitsui Fluorochemicals Co., Ltd.).

The method of applying the solution for forming a lubricating layer is not particularly limited, and examples thereof include a spin coating method, a spraying method, a paper coating method, and a dipping method.

When the dipping method is used, for example, the following method can be used. First, the substrate 11 in which respective layers up to the protective layer 17 are formed is immersed in the solution for forming a lubricating layer contained in an immersion vessel of a dip coating device. Next, the substrate 11 is lifted from the immersion vessel at a predetermined speed. Accordingly, the solution for forming a lubricating layer is applied to the surface of the protective layer 17 of the substrate 11.

When the dipping method is used, the solution for forming a lubricating layer can be uniformly applied to the surface of the protective layer 17, and the lubricating layer 18 with a uniform film thickness can be formed on the protective layer 17.

In the present embodiment, it is preferable to heat the substrate 11 in which the lubricating layer 18 is formed. When the heat treatment is performed, the adhesion between the lubricating layer 18 and the protective layer 17 is improved, and the adhesive force between the lubricating layer 18 and the protective layer 17 is improved.

The heat treatment temperature is preferably 100 to 180° C. When the heat treatment temperature is 100° C. or higher, an effect of improving the adhesion between the lubricating layer 18 and the protective layer 17 is sufficiently obtained. In addition, when the heat treatment temperature is 180° C. or lower, it is possible to prevent the thermal decomposition of the lubricating layer 18. The heat treatment time is preferably 10 to 120 minutes.

In the magnetic recording medium 10 of the present embodiment, at least the magnetic layer 16, the protective layer 17, and the lubricating layer 18 are sequentially provided on the substrate 11. In the magnetic recording medium 10 of the present embodiment, the lubricating layer 18 containing the above fluorine-containing ether compound is formed on and in contact with the protective layer 17. The lubricating layer 18 covers the surface of the protective layer 17 with a high coverage even if the thickness is thin. Therefore, the lubricating layer 18 in the magnetic recording medium 10 of the present embodiment has excellent wear resistance and spin-off resistance.

In addition, in the magnetic recording medium 10 of the present embodiment, the lubricating layer 18 covers the surface of the protective layer 17 with a high coverage. Therefore, environmental substances that generate contamination substances such as ionic impurities are prevented from entering through voids of the lubricating layer 18. Therefore, the magnetic recording medium 10 of the present embodiment has a small amount of contamination substances present on the surface. In addition, the lubricating layer 18 in the magnetic recording medium 10 of the present embodiment is less likely to generate foreign matter (smear) and can reduce the occurrence of pickup.

As described above, the magnetic recording medium 10 of the present embodiment has excellent reliability and durability.

EXAMPLES

Hereinafter, examples of the present invention will be described in more detail with reference to examples and comparative examples. Here, the present invention is not limited only to the following examples.

"Production of Lubricant"

Example 1

The compound represented by Formula (A) shown above was produced by the following method.

First, 4-aminobutanenitrile and di-tert-butyl dicarbonate were reacted in methanol to obtain a compound. Next, the obtained compound and epibromohydrin were reacted to synthesize a compound represented by the following Formula (20).

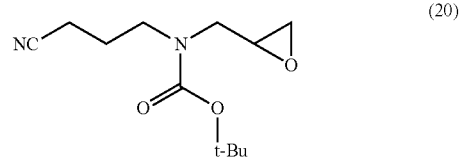 [SMILES: CC(C)(C)OC(=O)N(CCCC#N)CC1CO1]

(in Formula (20), t-Bu represents a tertiary butyl group).

Next, 20 g of a fluoropolyether (a number-average molecular weight of 1,000 and a molecular weight distribution of 1.1) represented by $HOCH_2CF_2O(CF_2CF_2O)_m(CF_2O)_nCF_2CH_2OH$ (in the formula, m indicating the average degree of polymerization is 4.5, and n indicating the average degree of polymerization is 4.5), 10.6 g (a molecular weight of 240.30, 44 mmol) of the compound represented by Formula (20), and 20 mL of t-butanol were put into a 200 mL eggplant flask under a nitrogen atmosphere, and the mixture was stirred at room temperature until it became uniform.

0.90 g (a molecular weight of 112.21, 8 mmol) of potassium tert-butoxide was added to this uniform solution and the mixture was stirred and reacted at 70° C. for 14 hours. The obtained reaction product was cooled to 25° C., neutralized with 1 mol/L hydrochloric acid, extracted with Vertel (registered trademark) XF, and washed with water. The organic layer was dehydrated with anhydrous sodium sulfate, the drying agent was filtered off, and the filtrate was then concentrated.

15 mL of trifluoroacetic acid was added to the concentrated filtrate, and the mixture was stirred and reacted at 25° C. for 3 hours. The reaction solution was transferred to a beaker containing 70 mL of 8% sodium bicarbonate water, and extracted twice with 200 mL of ethyl acetate. The organic layer was washed with water and dehydrated with anhydrous sodium sulfate. After the drying agent was filtered off, the filtrate was concentrated, and the residue was purified through silica gel column chromatography to obtain 12.8 g of a compound (A). In Formula (A), ma indicating the average degree of polymerization is 4.5, and na indicating the average degree of polymerization is 4.5.

The obtained compound (A) was subjected to $^1$H-NMR measurement, and the structure was identified based on the following results.

compound (A); $^1$H-NMR (CD$_3$COCD$_3$);
δ [ppm] 1.8 (4H), 2.5 (4H), 3.4 to 3.9 (22H)

Example 2

13.1 g of a compound (B) was obtained in the same operation as in Example 1 except that 11.2 g of the compound represented by the following Formula (21) was used in place of the compound represented by Formula (20). In Formula (B), mb indicating the average degree of polymerization is 4.5, and nb indicating the average degree of polymerization is 4.5.

The compound represented by Formula (21) was synthesized by reacting a compound, which was obtained by reacting 5-aminopentanenitrile and di-tert-butyl dicarbonate in methanol, with epibromohydrin.

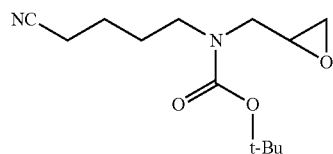

(21)

(in Formula (21), t-Bu represents a tertiary butyl group).
The obtained compound (B) was subjected to $^1$H-NMR measurement, and the structure was identified based on the following results.

compound (B); $^1$H-NMR (CD$_3$COCD$_3$);
δ [ppm] 1.6 to 2.0 (6H), 2.2 to 2.4 (2H), 2.5 (4H), 3.4 to 4.0 (22H)

Example 3

12.8 g of a compound (C) was obtained in the same operation as in Example 1 except that 10.6 g of the compound represented by the following Formula (22) was used in place of the compound represented by Formula (20). In Formula (C), mc indicating the average degree of polymerization is 4.5, and nc indicating the average degree of polymerization is 4.5.

The compound represented by Formula (22) was synthesized by protecting the amino group of 3-amino-2-methylpropanenitrile using di-tert-butyl dicarbonate and reacting it with epibromohydrin.

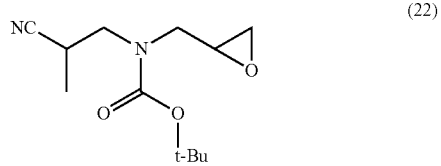 [SMILES: CC(C#N)CN(CC1CO1)C(=O)OC(C)(C)C]

(22)

(in Formula (22), t-Bu represents a tertiary butyl group).
The obtained compound (C) was subjected to $^1$H-NMR measurement, and the structure was identified based on the following results.

compound (C); $^1$H-NMR (CD$_3$COCD$_3$);
δ [ppm] 1.4 (6H), 3.4 to 4.0 (24H)

Example 4

14.3 g of a compound (D) was obtained in the same operation as in Example 1 except that 13.8 g of the compound represented by Formula (23) was used in place of the compound represented by Formula (20). In Formula (D), md indicating the average degree of polymerization is 4.5, and nd indicating the average degree of polymerization is 4.5.

The compound represented by Formula (23) was synthesized by reacting the compound represented by Formula (20) with glycidol.

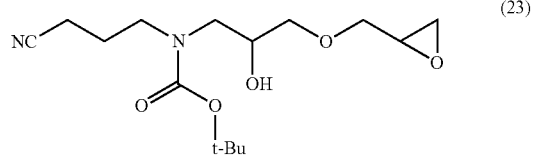 [SMILES: CC(C)(C)OC(=O)N(CCCC#N)CC(O)COCC1CO1]

(23)

(in Formula (23), t-Bu represents a tertiary butyl group).
The obtained compound (D) was subjected to $^1$H-NMR measurement, and the structure was identified based on the following results.

compound (D); $^1$H-NMR (CD$_3$COCD$_3$);
δ [ppm] 1.8 (4H), 2.5 (4H), 3.4 to 3.9 (34H)

Example 5

14.5 g of a compound (E) was obtained in the same operation as in Example 1 except that 18.8 g of the compound represented by Formula (24) was used in place of the compound represented by Formula (20). In Formula (E), me indicating the average degree of polymerization is 4.5, and ne indicating the average degree of polymerization is 4.5.

The compound represented by Formula (24) was synthesized by synthesizing a compound obtained by reacting the compound represented by Formula (20) with 3-butene-1-amine in which the amino group was protected using di-tert-butyl dicarbonate, and oxidizing the double bond of the obtained compound.

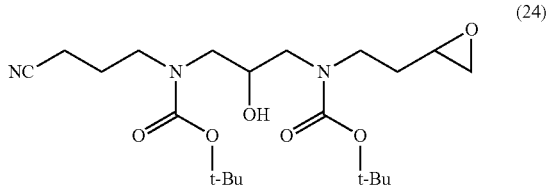 [SMILES: CC(C)(C)OC(=O)N(CCCC#N)CC(O)CN(CCC1CO1)C(=O)OC(C)(C)C]
(24)

(in Formula (24), t-Bu represents a tertiary butyl group).

The obtained compound (E) was subjected to $^1$H-NMR measurement, and the structure was identified based on the following results.

compound (E); $^1$H-NMR (CD$_3$COCD$_3$);

δ [ppm] 1.6 to 2.0 (10H), 2.2 to 2.4 (2H), 2.5 (4H), 3.4 to 3.9 (32H)

Example 6

14.5 g of a compound (F) was obtained in the same operation as in Example 1 except that 14.8 g of the compound represented by Formula (29) was used in place of the compound represented by Formula (20). In Formula (F), mf indicating the average degree of polymerization is 4.5, and nf indicating the average degree of polymerization is 4.5.

The compound represented by Formula (29) was synthesized by the following method.

First, 4-hydroxybutanenitrile and epibromohydrin were reacted to synthesize a compound represented by Formula (25). Next, the compound represented by Formula (25) and 2-propene-1-amine in which the amino group was protected using di-tert-butyl dicarbonate were reacted to synthesize a compound represented by Formula (26). Next, the compound represented by Formula (26) and pyridine and para-toluenesulfonyl chloride were reacted to synthesize a compound represented by Formula (27). Next, the compound represented by Formula (27) and trimethylsilyl cyanide and tetra-n-butylammonium fluoride were reacted to synthesize a compound represented by Formula (28). Then, the double bond of the compound represented by Formula (28) was oxidized to synthesize a compound represented by Formula (29).

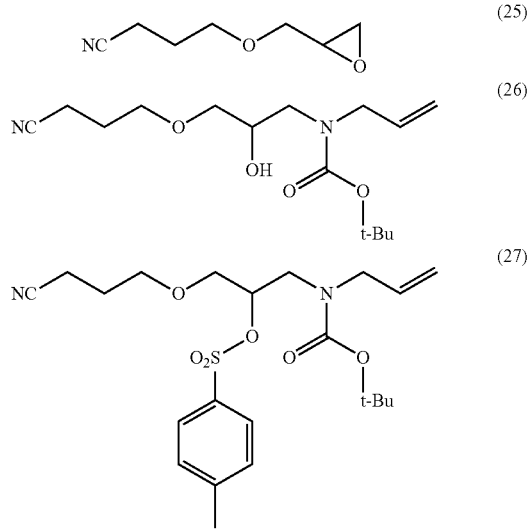
(25)
(26)
(27)

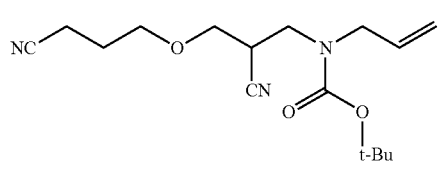
(28)

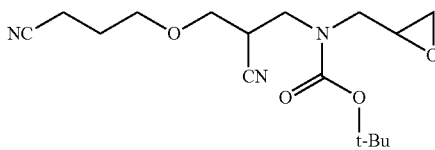
(29)

(in Formula (26) to Formula (29), t-Bu represents a tertiary butyl group).

The obtained compound (F) was subjected to $^1$H-NMR measurement, and the structure was identified based on the following results.

compound (F); $^1$H-NMR (CD$_3$COCD$_3$);

δ [ppm] 1.8 (4H), 2.5 (4H), 3.4 to 4.0 (32H)

Example 7

14.3 g of a compound (G) was obtained in the same operation as in Example 1 except that 18.1 g of the compound represented by Formula (31) was used in place of the compound represented by Formula (20). In Formula (G), mg indicating the average degree of polymerization is 4.5, and ng indicating the average degree of polymerization is 4.5.

The compound represented by Formula (31) was synthesized in the same synthesis operation as in the compound represented by Formula (29) except that the compound represented by Formula (30) was used in place of the compound represented by Formula (25).

The compound represented by Formula (30) was synthesized by reacting a compound, in which a hydroxyl group on one side of 1,3-propanediol was protected with dihydropyran, with epibromohydrin.

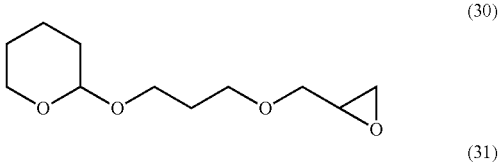
(30)

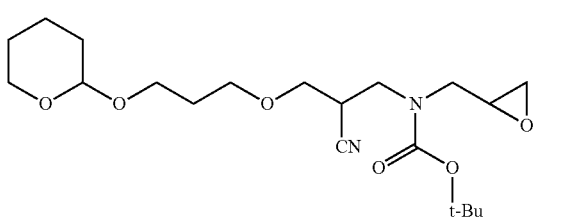
(31)

(in Formula (31), t-Bu represents a tertiary butyl group).

The obtained compound (G) was subjected to $^1$H-NMR measurement, and the structure was identified based on the following results.

compound (G); $^1$H-NMR (CD$_3$COCD$_3$);

δ [ppm] 1.8 (4H), 2.5 (4H), 3.4 to 4.0 (34H)

Example 8

The compound represented by Formula (H) was produced by the following method.

20.0 g of a fluoropolyether (a number-average molecular weight of 1,000 and a molecular weight distribution of 1.1) represented by $HOCH_2CF_2O(CF_2CF_2O)_m(CF_2O)_nCF_2CH_2OH$ (in the formula, m indicating the average degree of polymerization is 4.5, and n indicating the average degree of polymerization is 4.5), 2.88 g of the compound represented by Formula (20), and 12 mL of t-butanol were put into a 100 mL eggplant flask under a nitrogen gas atmosphere, and the mixture was stirred at room temperature until it became uniform. 0.674 g of potassium tert-butoxide was additionally added to this uniform solution and the mixture was stirred and reacted at 70° C. for 8 hours to obtain a reaction product.

The obtained reaction product was cooled to 25° C., neutralized with 0.5 mol/L of hydrochloric acid, and then extracted with Vertel (registered trademark) XF, and the organic layer was washed with water and dehydrated with anhydrous sodium sulfate. After the drying agent was filtered off, the filtrate was concentrated, and the residue was purified through silica gel column chromatography to obtain 9.93 g of a compound represented by the following Formula (32).

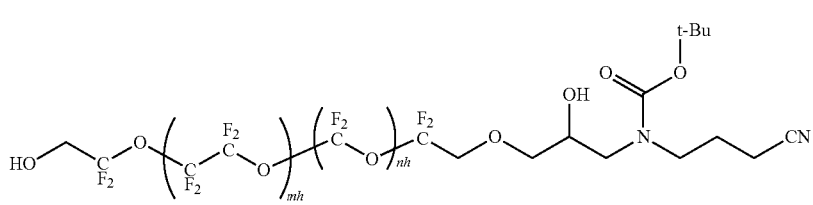

(32)

(in Formula (32), mh indicating the average degree of polymerization is 4.5, and nh indicating the average degree of polymerization is 4.5; and t-Bu represents a tertiary butyl group).

6.20 g of the compound represented by Formula (32), 1.21 g of a compound represented by the following Formula (33), and 50 mL of t-butanol were put into a 200 mL eggplant flask under a nitrogen gas atmosphere, and the mixture was stirred at room temperature until it became uniform. 0.168 g of potassium tert-butoxide was added to this uniform solution, and the mixture was stirred and reacted at 70° C. for 16 hours.

The compound represented by Formula (33) was synthesized by reacting a compound, in which a hydroxyl group on one side of ethylene glycol was protected with dihydropyran, with epibromohydrin.

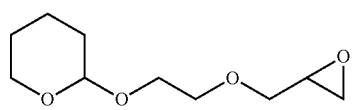

(33)

The solution after the reaction was completed was returned to room temperature, 20 g of a 10% hydrogen chloride/methanol solution (hydrogen chloride-methanol reagent (5-10%), commercially available from Tokyo Chemical Industry Co., Ltd.) was added, and the mixture was stirred at room temperature for 1 hour. The reaction solution was transferred to a beaker containing 70 mL of 8% sodium bicarbonate water and extracted twice with 200 mL of ethyl acetate. The organic layer was washed with water and dehydrated with anhydrous sodium sulfate. After the drying agent was filtered off, the filtrate was concentrated.

15 mL of trifluoroacetic acid was added to the concentrated filtrate, and the mixture was stirred and reacted at 25° C. for 3 hours. The reaction solution was transferred to a beaker containing 70 mL of 8% sodium bicarbonate water, and extracted twice with 200 mL of ethyl acetate. The organic layer was washed with water and dehydrated with anhydrous sodium sulfate. After the drying agent was filtered off, the filtrate was concentrated, and the residue was purified through silica gel column chromatography to obtain 4.40 g of a compound (H). In Formula (H), mh indicating the average degree of polymerization is 4.5, and nh indicating the average degree of polymerization is 4.5.

The obtained compound (H) was subjected to $^1$H-NMR measurement, and the structure was identified based on the following results.

compound (H); $^1$H-NMR ($CD_3COCD_3$);

δ [ppm] 1.8 (2H), 2.5 (2H), 3.4 to 4.2 (24H)

Example 9

4.81 g of a compound (I) was obtained in the same operation as in Example 8 except that 1.91 g of the compound represented by Formula (34) was used in place of the compound represented by Formula (33). In Formula (I), mi indicating the average degree of polymerization is 4.5, and ni indicating the average degree of polymerization is 4.5.

The compound represented by Formula (34) was synthesized by reacting a compound in which a hydroxyl group on one side of 1,3-propanediol was protected with dihydropyran with bis(2-oxiranylethyl)ether.

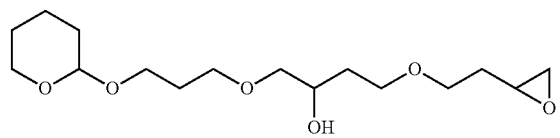

(34)

The obtained compound (I) was subjected to $^1$H-NMR measurement, and the structure was identified based on the following results.

compound (I); $^1$H-NMR ($CD_3COCD_3$);

δ [ppm] 1.6 to 2.0 (6H), 2.2 to 2.4 (2H), 2.5 (2H), 3.3 to 4.2 (30H)

Example 10

4.53 g of a compound (J) was obtained in the same operation as in Example 8 except that 1.52 g of the compound represented by Formula (35) was used in place of the compound represented by Formula (33). In Formula (J), mj indicating the average degree of polymerization is 4.5, and nj indicating the average degree of polymerization is 4.5.

The compound represented by Formula (35) was synthesized by reacting a compound obtained by reacting 4-aminobutanenitrile and di-tert-butyl dicarbonate in methanol with 2-(2-bromoethyl)oxirane.

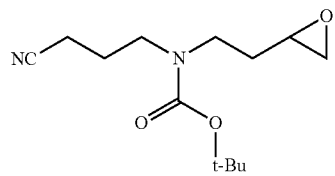

(35)

(in Formula (35), t-Bu represents a tertiary butyl group).

The obtained compound (J) was subjected to $^1$H-NMR measurement, and the structure was identified based on the following results.

compound (J); $^1$H-NMR (CD$_3$COCD$_3$);

δ [ppm] 1.6 to 2.0 (5H), 2.2 to 2.4 (1H), 2.5 (4H), 3.3 to 4.2 (22H)

Example 11

4.98 g of a compound (K) was obtained in the same operation as in Example 8 except that 2.81 g of the compound represented by Formula (40) was used in place of the compound represented by Formula (33). In Formula (K), mk indicating the average degree of polymerization is 4.5, and nk indicating the average degree of polymerization is 4.5.

The compound represented by Formula (40) was synthesized by the following method.

First, the double bond on one side of a compound obtained by reacting di-4-pentenylamine and di-tert-butyl dicarbonate in methanol was oxidized to synthesize a compound represented by Formula (36). Next, the compound represented by Formula (36) and a compound in which a hydroxyl group on one side of 1,4-butanediol was protected with dihydropyran were reacted to synthesize a compound represented by Formula (37). Next, the compound represented by Formula (37), pyridine and paratoluenesulfonyl chloride were reacted to synthesize a compound represented by Formula (38). Next, the compound represented by Formula (38), trimethylsilyl cyanide and tetra-n-butylammonium fluoride were reacted to synthesize a compound represented by Formula (39). Then, the double bond of the compound represented by Formula (39) was oxidized to synthesize a compound represented by Formula (40).

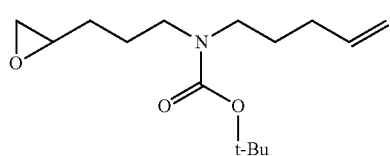

(36)

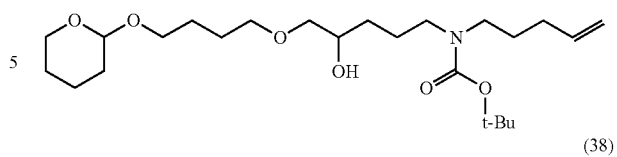

(37)

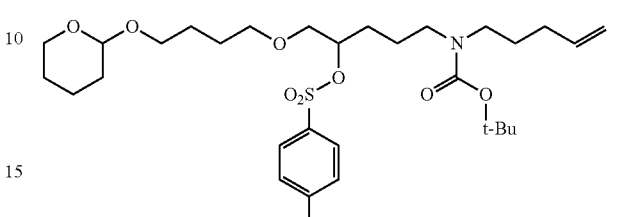

(38)

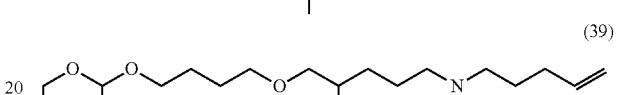

(39)

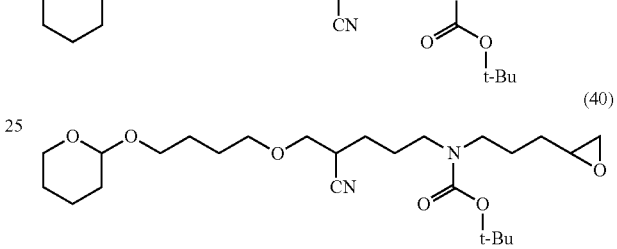

(40)

(in Formula (36) to Formula (40), t-Bu represents a tertiary butyl group).

The obtained compound (K) was subjected to $^1$H-NMR measurement, and the structure was identified based on the following results.

compound (K); $^1$H-NMR (CD$_3$COCD$_3$);

δ [ppm] 1.6 to 2.0 (8H), 2.2 to 2.4 (2H), 2.5 (2H), 3.3 to 4.2 (34H)

Example 12

4.87 g of a compound (L) was obtained in the same operation as in Example 8 except that 2.11 g of the compound represented by Formula (45) was used in place of the compound represented by Formula (33). In Formula (L), ml indicating the average degree of polymerization is 4.5, and nl indicating the average degree of polymerization is 4.5.

The compound represented by Formula (45) was synthesized by the following method.

First, the double bond on one side of a compound obtained by reacting di-3-butenylamine and di-tert-butyl dicarbonate in methanol was oxidized to synthesize a compound represented by Formula (41). Next, the compound represented by Formula (41) and 4-hydroxybutanenitrile were reacted to synthesize a compound represented by Formula (42). Next, the compound represented by Formula (42), pyridine and paratoluenesulfonyl chloride were reacted to synthesize a compound represented by Formula (43). Next, the compound represented by Formula (43), trimethylsilyl cyanide and tetra-n-butylammonium fluoride were reacted to synthesize a compound represented by Formula (44). Then, the double bond of the compound represented by Formula (44) was oxidized to synthesize a compound represented by Formula (45).

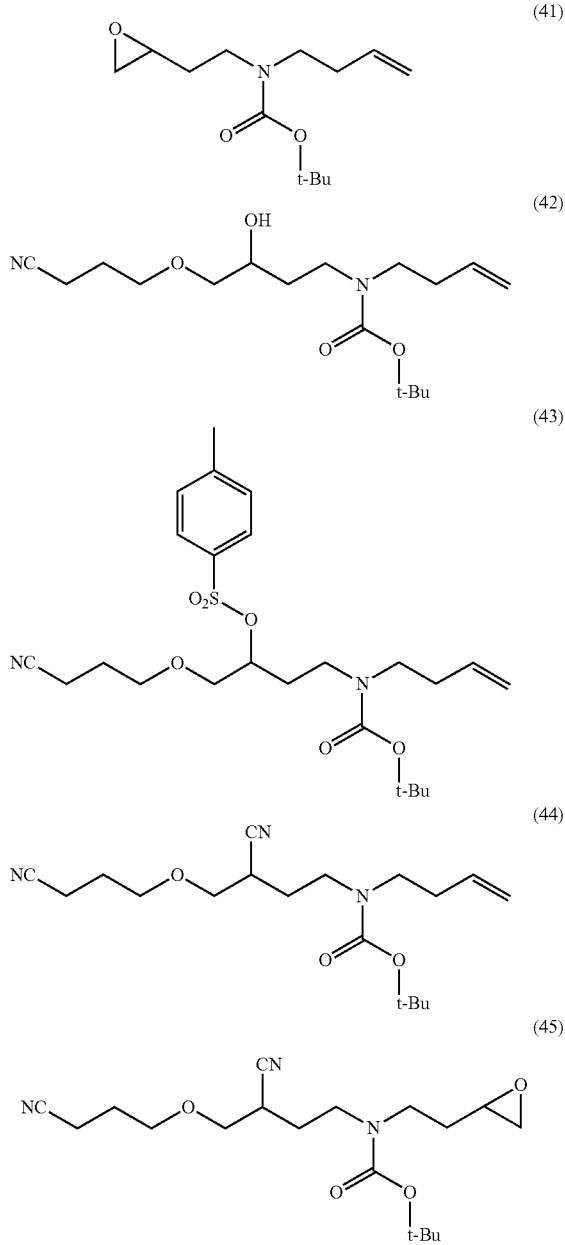

(in Formula (41) to Formula (45), t-Bu represents a tertiary butyl group).

The obtained compound (L) was subjected to ¹H-NMR measurement, and the structure was identified based on the following results.

compound (L); ¹H-NMR (CD₃COCD₃);

δ [ppm] 1.6 to 2.0 (6H), 2.2 to 2.4 (2H), 2.5 (2H), 3.3 to 4.2 (29H)

Example 13

4.43 g of a compound (M) was obtained in the same operation as in Example 8 except that 2.35 g of the compound represented by Formula (46) was used in place of the compound represented by Formula (33). In Formula (M), mm indicating the average degree of polymerization is 4.5, and nm indicating the average degree of polymerization is 4.5.

The compound represented by Formula (46) was synthesized by reacting a compound obtained by reacting propargylamine and di-tert-butyl dicarbonate in methanol with 2-(2-bromoethyl)oxirane.

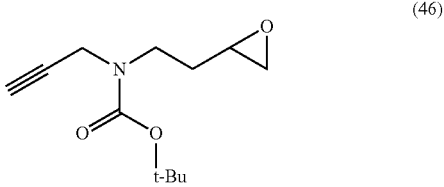 [SMILES: C#CCN(CCC1CO1)C(=O)OC(C)(C)C]

(in Formula (46), t-Bu represents a tertiary butyl group).

The obtained compound (M) was subjected to ¹H-NMR measurement, and the structure was identified based on the following results.

Compound (M); ¹H-NMR (CD₃COCD₃);

δ [ppm] 1.6 to 2.0 (3H), 2.2 to 2.4 (1H), 2.5 (2H), 2.7 (1H), 3.3 to 4.2 (22H)

Example 14

4.39 g of a compound (N) was obtained in the same operation as in Example 8 except that 1.29 g of the compound represented by Formula (47) was used in place of the compound represented by Formula (33). In Formula (N), mn indicating the average degree of polymerization is 4.5, and nn indicating the average degree of polymerization is 4.5.

The compound represented by Formula (47) was synthesized by reacting a compound obtained by reacting 1-propylamine and di-tert-butyl dicarbonate in methanol with epibromohydrin.

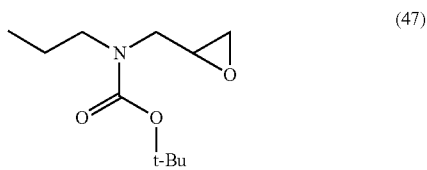

(in Formula (47), t-Bu represents a tertiary butyl group).

The obtained compound (N) was subjected to ¹H-NMR measurement, and the structure was identified based on the following results.

compound (N); ¹H-NMR (CD₃COCD₃);

δ [ppm] 0.9 to 1.1 (5H), 1.8 (2H), 2.5 (2H), 3.4 to 4.2 (22H)

Example 15

4.62 g of a compound (O) was obtained in the same operation as in Example 8 except that 1.67 g of the compound represented by Formula (48) was used in place of the compound represented by Formula (33). In Formula (0), mo indicating the average degree of polymerization is 4.5, and no indicating the average degree of polymerization is 4.5.

The compound represented by Formula (48) was synthesized by reacting a compound obtained by reacting p-anisidine and di-tert-butyl dicarbonate in methanol with epibromohydrin.

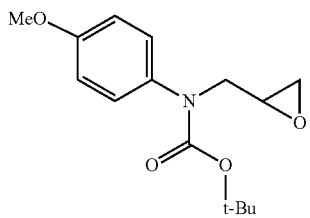

(in Formula (48), t-Bu represents a tertiary butyl group and Me represents a methyl group).

The obtained compound (O) was subjected to $^1$H-NMR measurement, and the structure was identified based on the following results.

compound (O); $^1$H-NMR (CD$_3$COCD$_3$);

δ [ppm] 1.8 (2H), 2.5 (2H), 2.7 (1H), 3.3 to 4.2 (21H), 6.8 (4H), 7.4 (1H)

Example 16

4.64 g of a compound (P) was obtained in the same operation as in Example 8 except that 2.32 g of the compound represented by Formula (49) was used in place of the compound represented by Formula (33). In Formula (P), mp indicating the average degree of polymerization is 4.5, and np indicating the average degree of polymerization is 4.5.

The compound represented by Formula (49) was synthesized by the following method. Allylamine and di-tert-butyl dicarbonate were reacted in methanol to obtain a first compound. The obtained first compound, sodium hydroxide and epibromohydrin were reacted to obtain a second compound. Next, the double bond on one side of the second compound was oxidized. Through the above processes, the compound represented by Formula (49) was obtained.

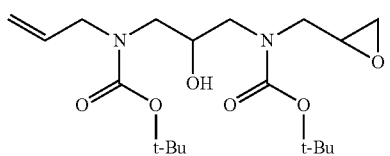

(in Formula (49), t-Bu represents a tertiary butyl group).

The obtained compound (P) was subjected to $^1$H-NMR measurement, and the structure was identified based on the following results.

compound (P); $^1$H-NMR (CD$_3$COCD$_3$);

δ [ppm] 1.8 (2H), 2.5 (2H), 3.3 to 4.2 (29H), 5.1 to 5.2 (1H), 5.8 to 6.0 (1H), 7.4 (1H)

Example 17

4.77 g of a compound (Q) was obtained in the same operation as in Example 8 except that 2.54 g of the compound represented by Formula (53) was used in place of the compound represented by Formula (33). In Formula (Q), mq indicating the average degree of polymerization is 4.5, and nq indicating the average degree of polymerization is 4.5.

The compound represented by Formula (53) was synthesized by the following method.

First, a compound obtained by reacting 3-butenylamine and di-tert-butyl dicarbonate in methanol, sodium hydroxide and epibromohydrin were reacted to synthesize a compound represented by Formula (50). Next, the compound represented by Formula (50), pyridine and paratoluenesulfonyl chloride were reacted to synthesize a compound represented by Formula (51). Next, the compound represented by Formula (51), trimethylsilyl cyanide and tetra-n-butylammonium fluoride were reacted to synthesize a compound represented by Formula (52). Then, the double bond on one side of the compound represented by Formula (52) was oxidized to synthesize a compound represented by Formula (53).

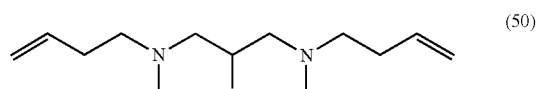

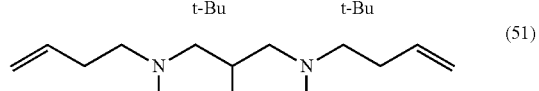

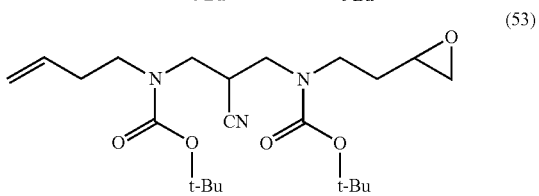

(in Formula (50) to Formula (53), t-Bu represents a tertiary butyl group).

The obtained compound (Q) was subjected to $^1$H-NMR measurement, and the structure was identified based on the following results.

compound (Q); $^1$H-NMR (CD$_3$COCD$_3$);

δ [ppm] 1.6 to 2.0 (5H), 2.2 to 2.4 (1H), 2.5 (2H), 3.3 to 4.2 (28H), 5.1 to 5.2 (1H), 5.8 to 6.0 (1H), 7.4 (1H)

Example 18

5.00 g of a compound (R) was obtained in the same operation as in Example 8 via the intermediate represented by Formula (54) except that 1.69 g of the compound represented by Formula (25) was used in place of the compound represented by Formula (20) and 2.32 g of the compound represented by Formula (55) was used in place of the compound represented by Formula (33). In Formula (R), mr indicating the average degree of polymerization is 4.5, and nr indicating the average degree of polymerization is 4.5.

The compound represented by Formula (55) was synthesized by reacting a compound obtained by oxidizing the double bond of the compound represented by Formula (26) with glycidol.

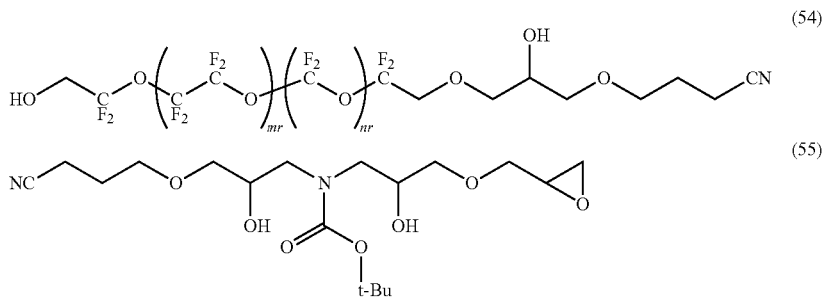

(in Formula (54), mr indicating the average degree of polymerization is 4.5, and nr indicating the average degree of polymerization is 4.5).

(in Formula (55), t-Bu represents a tertiary butyl group).

The obtained compound (R) was subjected to $^1$H-NMR measurement, and the structure was identified based on the following results.

compound (R); $^1$H-NMR (CD$_3$COCD$_3$); δ [ppm] 1.8 (4H), 3.3 to 4.2 (37H)

Example 19

5.08 g of a compound (S) was obtained in the same operation as in Example 18 except that 2.97 g of the compound represented by Formula (60) was used in place of the compound represented by Formula (55). In Formula (S), ms indicating the average degree of polymerization is 4.5, and ns indicating the average degree of polymerization is 4.5.

The compound represented by Formula (60) was synthesized by the following method.

First, a compound, which was obtained by reacting a compound in which a hydroxyl group of 2-aminoethanol was protected with dihydropyran and di-tert-butyl dicarbonate in methanol, and bis(2-oxiranylethyl)ether were reacted to synthesize a compound represented by Formula (56). Next, the compound represented by Formula (56) and allyl alcohol were reacted to synthesize a compound represented by Formula (57). Next, the compound represented by Formula (57), pyridine and paratoluenesulfonyl chloride were reacted to synthesize a compound represented by Formula (58). Next, the compound represented by Formula (58), trimethylsilyl cyanide and tetra-n-butylammonium fluoride were reacted to synthesize a compound represented by Formula (59). Then, the double bond of the compound represented by Formula (59) was oxidized to synthesize a compound represented by Formula (60).

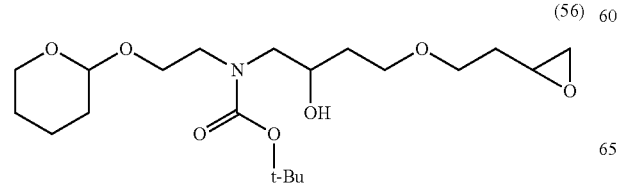

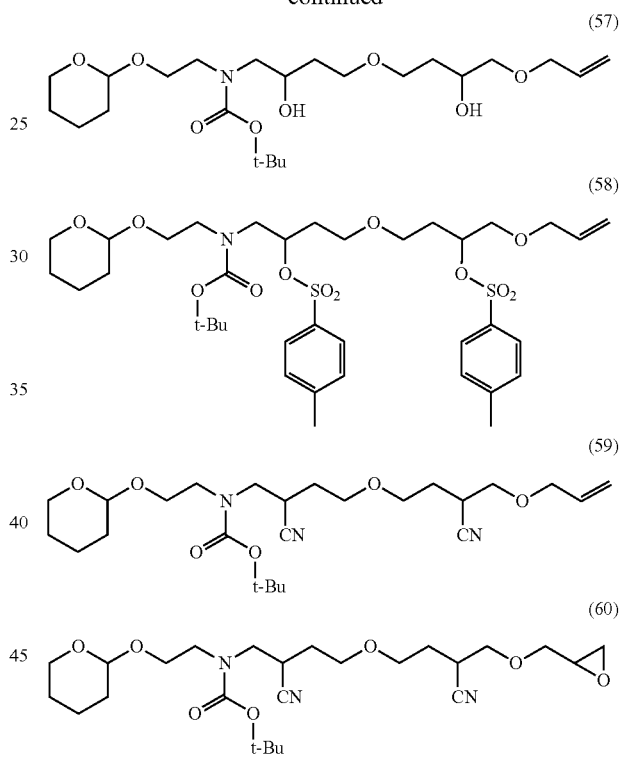

(in Formula (56) to Formula (60), t-Bu represents a tertiary butyl group).

The obtained compound (S) was subjected to $^1$H-NMR measurement, and the structure was identified based on the following results.

compound (S); $^1$H-NMR (CD$_3$COCD$_3$);

δ [ppm] 1.6 to 2.0 (4H), 2.2 to 2.4 (2H), 3.3 to 4.2 (36H)

Example 20

5.18 g of a compound (T) was obtained in the same operation as in Example 18 except that 2.63 g of the compound represented by Formula (65) was used in place of the compound represented by Formula (55). In Formula (T), mt indicating the average degree of polymerization is 4.5, and nt indicating the average degree of polymerization is 4.5.

The compound represented by Formula (65) was synthesized by the following method.

First, allyl alcohol and 2-(3-bromopropyl)oxirane were reacted to synthesize a compound represented by Formula (61). Next, a compound obtained by reacting 4-aminobutanenitrile and di-tert-butyl dicarbonate in methanol and the compound represented by Formula (61) were reacted to synthesize a compound represented by Formula (62). Next, the compound represented by Formula (62), pyridine and paratoluenesulfonyl chloride were reacted to synthesize a compound represented by Formula (63). Next, the compound represented by Formula (63), trimethylsilyl cyanide and tetra-n-butylammonium fluoride were reacted to synthesize a compound represented by Formula (64). Then, the double bond of the compound represented by Formula (64) was oxidized and reacted with 2-(hydroxyethyl)oxirane to synthesize a compound represented by Formula (65).

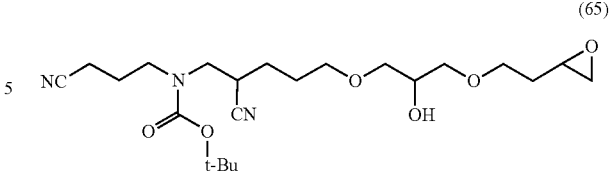

(in Formula (62) to Formula (65), t-Bu represents a tertiary butyl group).

The obtained compound (T) was subjected to $^1$H-NMR measurement, and the structure was identified based on the following results.

compound (T); $^1$H-NMR (CD$_3$COCD$_3$);

δ [ppm] 1.6 to 2.0 (7H), 2.2 to 2.4 (1H), 2.5 (2H), 3.4 to 4.0 (36H)

Example 21

4.62 g of a compound (U) was obtained in the same operation as in Example 8 via the intermediate represented by Formula (70) except that 13.69 g of the compound represented by Formula (69) was used in place of the compound represented by Formula (20) and 1.28 g of the compound represented by Formula (71) was used in place of the compound represented by Formula (33). In Formula (U), mu indicating the average degree of polymerization is 4.5, and nu indicating the average degree of polymerization is 4.5.

The compound represented by Formula (69) was synthesized by the following method.

First, a compound, which was obtained by reacting 2-(aminomethyl)butane-1,4-diol and di-tert-butyl dicarbonate in methanol, and 4-bromo-1-butene were reacted to synthesize a compound represented by Formula (66). Next, the compound represented by Formula (66), pyridine and paratoluenesulfonyl chloride were reacted to synthesize a compound represented by Formula (67). Next, the compound represented by Formula (67), trimethylsilyl cyanide and tetra-n-butylammonium fluoride were reacted to synthesize a compound represented by Formula (68). Then, the double bond of the compound represented by Formula (68) was oxidized to synthesize a compound represented by Formula (69).

The compound represented by Formula (71) was synthesized by synthesizing a compound, which was obtained by reacting diallylamine and di-tert-butyl dicarbonate in methanol, and oxidizing the double bond on one side of the obtained compound.

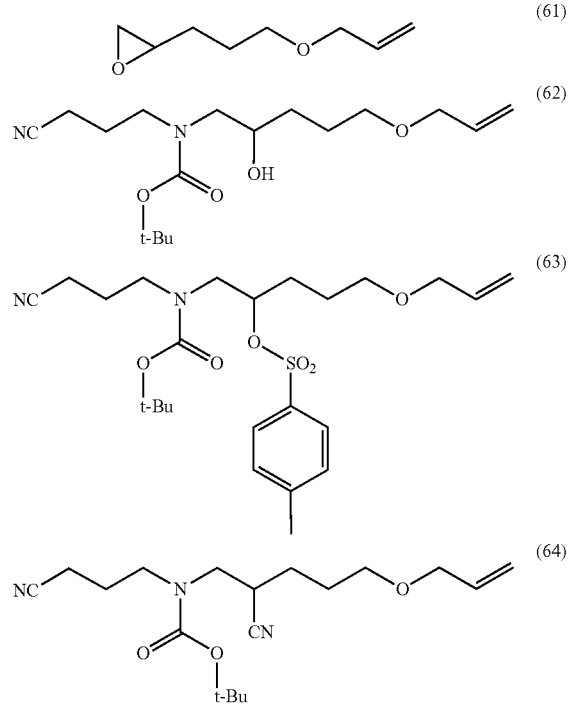

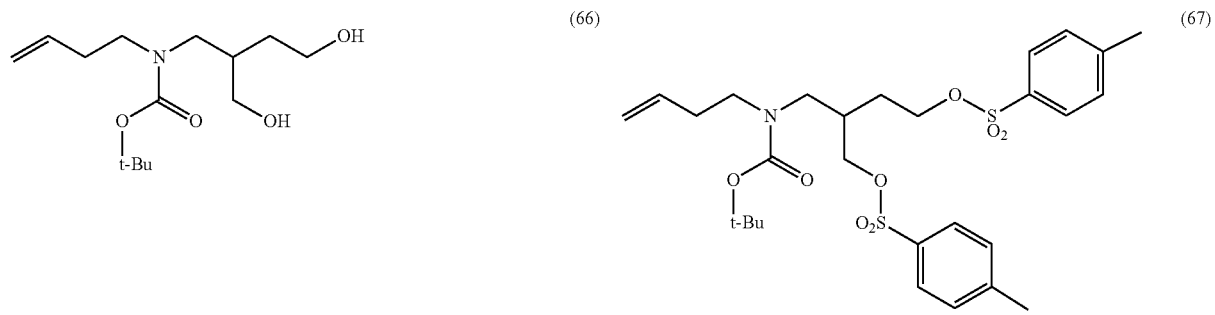

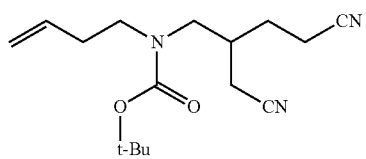 (68)

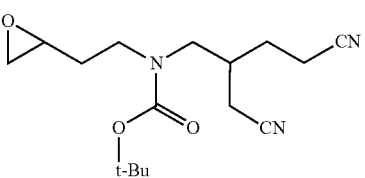 (69)

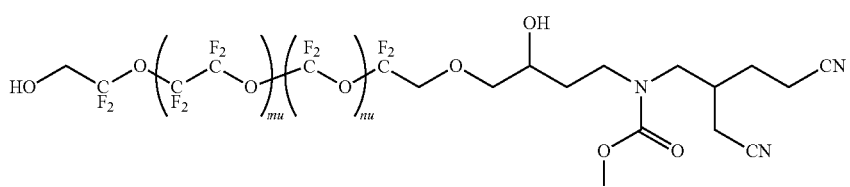 (70)

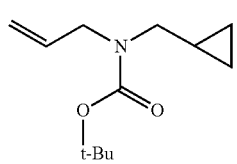 (71)

(in Formula (66) to Formula (71), t-Bu represents a tertiary butyl group).

(in Formula (70), mu indicating the average degree of polymerization is 4.5, and nu indicating the average degree of polymerization is 4.5).

The obtained compound (U) was subjected to $^1$H-NMR measurement, and the structure was identified based on the following results.

compound (U); $^1$H-NMR (CD$_3$COCD$_3$);

δ [ppm] 1.6 to 2.0 (4H), 2.2 to 2.4 (1H), 3.4 to 3.9 (26H), 5.1 to 5.2 (1H), 5.2 to 5.3 (1H), 5.8 to 6.0 (1H)

Example 22

4.97 g of a compound (V) was obtained in the same operation as in Example 21 except that 2.93 g of the compound represented by Formula (73) was used in place of the compound represented by Formula (71). In Formula (V), my indicating the average degree of polymerization is 4.5, and nv indicating the average degree of polymerization is 4.5.

The compound represented by Formula (73) was synthesized by reacting the compound represented by Formula (72) with allyl alcohol. The compound represented by Formula (72) was synthesized by oxidizing the double bond of the compound represented by Formula (50).

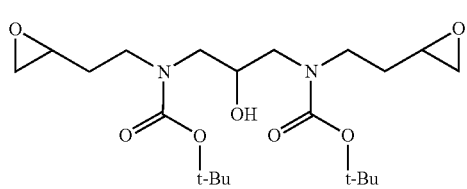 (72)

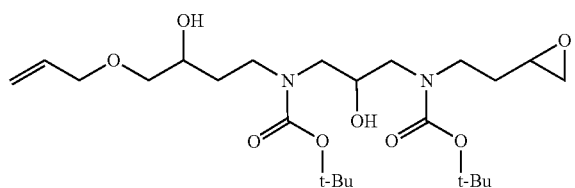 (73)

(in Formula (72) and Formula (73), t-Bu represents a tertiary butyl group).

The obtained compound (V) was subjected to $^1$H-NMR measurement, and the structure was identified based on the following results.

compound (V); $^1$H-NMR (CD$_3$COCD$_3$);

δ [ppm] 3.4 to 3.9 (25H), 5.1 to 5.2 (1H), 5.2 to 5.3 (1H), 5.8 to 6.0 (1H)

Example 23

4.61 g of a compound represented by Formula (W) was obtained in the same operation as in Example 16 via the compound represented by the following Formula (74) as an intermediate except that, in place of a fluoropolyether represented by HOCH$_2$CF$_2$O(CF$_2$CF$_2$O)$_m$(CF$_2$O)$_n$CF$_2$CH$_2$OH (in the formula, m indicating the average degree of polymerization is 4.5, and n indicating the average degree of polymerization is 4.5), a fluoropolyether represented by HOCH$_2$CF$_2$O(CF$_2$CF$_2$O)$_w$CF$_2$CH$_2$OH (in the formula, w indicating the average degree of polymerization is 7.0) was used. In Formula (W), w indicating the average degree of polymerization is 7.0.

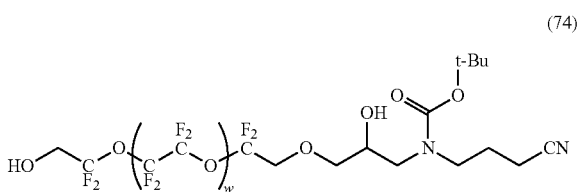

(74)

(in Formula (74), w indicating the average degree of polymerization is 7.0; and t-Bu represents a tertiary butyl group).

The obtained compound (W) was subjected to $^1$H-NMR measurement, and the structure was identified based on the following results.

compound (W); $^1$H-NMR (CD$_3$COCD$_3$);

δ [ppm] 1.8 (2H), 2.5 (2H), 3.3 to 4.2 (29H), 5.1 to 5.2 (1H), 5.8 to 6.0 (1H), 7.4 (1H)

Example 24

4.54 g of a compound represented by Formula (X) was obtained in the same operation as in Example 16 via the compound represented by the following Formula (75) as an intermediate except that, in place of a fluoropolyether represented by HOCH$_2$CF$_2$O(CF$_2$CF$_2$O)$_m$(CF$_2$O)$_n$CF$_2$CH$_2$OH (in the formula, m indicating the average degree of polymerization is 4.5, and n indicating the average degree of polymerization is 4.5), a fluoropolyether represented by HOCH$_2$CF$_2$CF$_2$O(CF$_2$CF$_2$CF$_2$O)$_x$CF$_2$CF$_2$CH$_2$OH (in the formula, x indicating the average degree of polymerization is 4.5) was used. In Formula (X), x indicating the average degree of polymerization is 4.5.

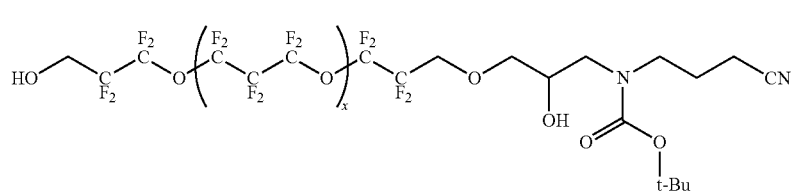

(75)

(in Formula (75), x indicating the average degree of polymerization is 4.5 and t-Bu represents a tertiary butyl group).

The obtained compound (X) was subjected to $^1$H-NMR measurement, and the structure was identified based on the following results.

compound (X); $^1$H-NMR (CD$_3$COCD$_3$);

δ [ppm] 1.8 (2H), 2.5 (2H), 3.3 to 4.2 (29H), 5.1 to 5.2 (1H), 5.8 to 6.0 (1H), 7.4 (1H)

Example 25

4.53 g of a compound represented by Formula (Y) was obtained in the same operation as in Example 16 via the compound represented by the following Formula (76) as an intermediate except that, in place of a fluoropolyether represented by HOCH$_2$CF$_2$O(CF$_2$CF$_2$O)$_m$(CF$_2$O)$_n$CF$_2$CH$_2$OH (in the formula, m indicating the average degree of polymerization is 4.5, and n indicating the average degree of polymerization is 4.5), a fluoropolyether represented by HOCH$_2$CF$_2$CF$_2$CF$_2$O(CF$_2$CF$_2$CF$_2$CF$_2$O)$_y$CF$_2$CF$_2$CF$_2$CH$_2$OH (in the formula, y indicating the average degree of polymerization is 3.0) was used. In Formula (Y), y indicating the average degree of polymerization is 3.0.

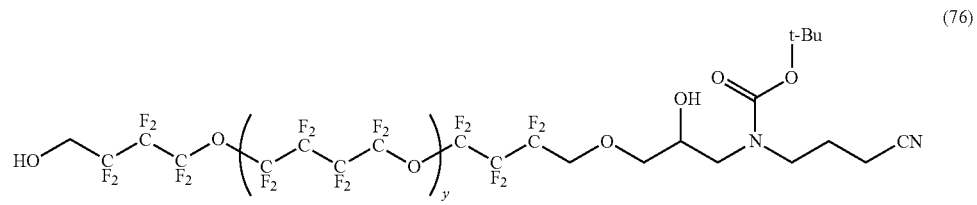

(76)

(in Formula (76), y indicating the average degree of polymerization is 3.0 and t-Bu represents a tertiary butyl group).

The obtained compound (Y) was subjected to $^1$H-NMR measurement, and the structure was identified based on the following results.

compound (Y); $^1$H-NMR (CD$_3$COCD$_3$);

δ [ppm] 1.8 (2H), 2.5 (2H), 3.3 to 4.2 (29H), 5.1 to 5.2 (1H), 5.8 to 6.0 (1H), 7.4 (1H)

Example 26

4.57 g of a compound represented by Formula (Z) was obtained in the same operation as in Example 16 via the compound represented by the following Formula (77) as an intermediate, except that, in place of a fluoropolyether represented by HOCH$_2$CF$_2$O(CF$_2$CF$_2$O)$_m$(CF$_2$O)$_n$CF$_2$CH$_2$OH (in the formula, m indicating the average degree of polymerization is 4.5, and n indicating the average degree of polymerization is 4.5), a fluoropolyether represented by HOCH$_2$CF(CF$_3$)(OCF(CF$_3$)CF$_2$)$_z$OCF(CF$_3$)CH$_2$OH (in the formula, z indicating the average degree of polymerization is 4.5) was used. In Formula (Z), z indicating the average degree of polymerization is 4.5.

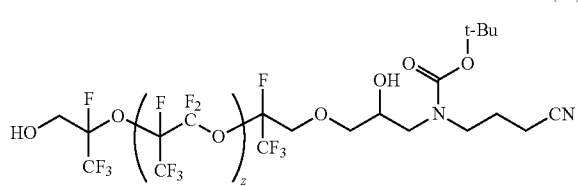

(77)

(in Formula (77), z indicating the average degree of polymerization is 4.5 and t-Bu represents a tertiary butyl group).

The obtained compound (Z) was subjected to $^1$H-NMR measurement, and the structure was identified based on the following results.

compound (Z); $^1$H-NMR (CD$_3$COCD$_3$);

δ [ppm] 1.8 (2H), 2.5 (2H), 3.3 to 4.2 (29H), 5.1 to 5.2 (1H), 5.8 to 6.0 (1H), 7.4 (1H)

Table 1 to Table 3 show the structures of the terminal group represented by $R^1$, the linking group represented by $R^2$ (in Formula (2), X in [A] and X in [B]), the PFPR chain represented by $R^3$, the linking group represented by $R^4$ (in Formula (3), X in [C] and X in [D]), and the terminal group represented by $R^5$ when the compounds of Examples 1 to 26 obtained in this manner were applied to Formula (1).

In Table 1 to Table 3, when $R^2$ in the compounds of Examples 1 to 26 has a total of two or more [A] and [B] in Formula (2), [A] or [B] closest to the $R^3$ side is listed at the top, and the others in order from the $R^3$ side to the $R^1$ side are listed therebelow in this order. In addition, when $R^4$ in the compounds of Examples 1 to 26 has a total of two or more [C] and [D] in Formula (3), [C] or [D] closest to the $R^3$ side is listed at the top, and the others in order from the $R^3$ side to the $R^5$ side are listed therebelow in this order.

In addition, Table 1 to Table 3 show the number of secondary amines [—NH—], the number of hydroxyl groups [—OH], and the number of cyano groups [—CN] contained in the molecules of the compounds of Examples 1 to 26, and the total number of secondary amines [—NH—], hydroxyl groups [—OH] and cyano groups [—CN] contained the molecules.

TABLE 1

| Compound | | $R^1$ | $R^2$ | $R^3$ | $R^4$ | $R^5$ | Number of [—NH—]'s | Number of [—OH]'s | Number of [—CN]'s | Total number of [—NH—]'s, [—OH]'s and [—CN]'s |
|---|---|---|---|---|---|---|---|---|---|---|
| Example 1 | (A) | 3-cyanopropyl | [A]X=NH | Formula (6) | [C]X=NH | same as $R^1$ | 2 | 2 | 2 | 6 |
| Example 2 | (B) | 4-cyanobutyl | [A]X=NH | Formula (6) | [C]X=NH | same as $R^1$ | 2 | 2 | 2 | 6 |
| Example 3 | (C) | 2-cyanopropyl | [A]X=NH | Formula (6) | [C]X=NH | same as $R^1$ | 2 | 2 | 2 | 6 |
| Example 4 | (D) | 3-cyanopropyl | [A]X=O [A]X=NH | Formula (6) | [C]X=O [C]X=NH | same as $R^1$ | 2 | 4 | 2 | 8 |
| Example 5 | (E) | 3-cyanopropyl | [A]X=NH [A]X=NH | Formula (6) | [C]X=NH [C]X=NH | same as $R^1$ | 4 | 4 | 2 | 10 |
| Example 6 | (F) | 3-cyanopropyl | [A]X=NH [B]X=O | Formula (6) | [C]X=NH [D]X=O | same as $R^1$ | 2 | 2 | 4 | 8 |
| Example 7 | (G) | 3-hydroxypropyl | [A]X=NH [B]X=O | Formula (6) | [C]X=NH [D]X=O | same as $R^1$ | 2 | 4 | 2 | 8 |
| Example 8 | (H) | 2-hydroxyethyl | [A]X=O | Formula (6) | [C]X=NH | 3-cyanopropyl | 1 | 3 | 1 | 5 |
| Example 9 | (I) | 3-hydroxypropyl | [A]X=O [A]X=O | Formula (6) | [C]X=NH | 3-cyanopropyl | 1 | 4 | 1 | 6 |

TABLE 2

| Compound | | $R^1$ | $R^2$ | $R^3$ | $R^4$ | $R^5$ | Number of [—NH—]'s | Number of [—OH]'s | Number of [—CN]'s | Total number of [—NH—]'s, [—OH]'s and [—CN]'s |
|---|---|---|---|---|---|---|---|---|---|---|
| Example 10 | (J) | 3-cyanopropyl | [A]X=NH | Formula (6) | [C]X=NH | same as $R^1$ | 2 | 2 | 2 | 6 |
| Example 11 | (K) | 4-hydroxybutyl | [A]X=NH [B]X=O | Formula (6) | [C]X=NH | 3-cyanopropyl | 2 | 3 | 2 | 7 |
| Example 12 | (L) | 3-cyanopropyl | [A]X=NH [B]X=O | Formula (6) | [C]X=NH | same as $R^1$ | 2 | 2 | 3 | 7 |
| Example 13 | (M) | 2-propynyl | [A]X=NH | Formula (6) | [C]X=NH | 3-cyanopropyl | 2 | 2 | 1 | 5 |
| Example 14 | (N) | propyl | [A]X=NH | Formula (6) | [C]X=NH | 3-cyanopropyl | 2 | 2 | 1 | 5 |
| Example 15 | (O) | 4-methoxyphenyl | [A]X=NH | Formula (6) | [C]X=NH | 3-cyanopropyl | 2 | 2 | 1 | 5 |

TABLE 2-continued

| | Compound | R¹ | R² | R³ | R⁴ | R⁵ | Number of [—NH—]'s | Number of [—OH]'s | Number of [—CN]'s | Total number of [—NH—]'s, [—OH]'s and [—CN]'s |
|---|---|---|---|---|---|---|---|---|---|---|
| Example 16 | (P) | allyl | [A]X=NH [A]X=NH | Formula (6) | [C]X=NH | 3-cyanopropyl | 3 | 3 | 1 | 7 |
| Example 17 | (Q) | 3-butenyl | [A]X=NH [B]X=NH | Formula (6) | [C]X=NH | 3-cyanopropyl | 3 | 2 | 2 | 7 |
| Example 18 | (R) | 3-cyanopropyl | [A]X=O [A]X=NH | Formula (6) | [C]X=O | same as R¹ | 1 | 4 | 2 | 7 |

TABLE 3

| | Compound | R¹ | R² | R³ | R⁴ | R⁵ | Number of [—NH—]'s | Number of [—OH]'s | Number of [—CN]'s | Total number of [—NH—]'s, [—OH]'s and [—CN]'s |
|---|---|---|---|---|---|---|---|---|---|---|
| Example 19 | (S) | 2-hydroxyethyl | [A]X=O [B]X=O [B]X=NH | Formula (6) | [C]X=O | 3-cyanopropyl | 1 | 3 | 3 | 7 |
| Example 20 | (T) | 3-cyanopropyl | [A]X=O [A]X=O [B]X=NH | Formula (6) | [C]X=O | same as R¹ | 1 | 3 | 3 | 7 |
| Example 21 | (U) | allyl | [A]X=NH | Formula (6) | [C]X=NH | 4-cyano-2-(cyanomethyl)butyl | 2 | 2 | 2 | 6 |
| Example 22 | (V) | allyl | [A]X=NH [A]X=NH [A]X=O | Formula (6) | [C]X=NH | 4-cyano-2-(cyanomethyl)butyl | 3 | 4 | 2 | 9 |
| Example 23 | (W) | allyl | [A]X=NH [A]X=NH | Formula (7) | [C]X=NH | 3-cyanopropyl | 3 | 3 | 1 | 7 |
| Example 24 | (X) | allyl | [A]X=NH [A]X=NH | Formula (8) | [C]X=NH | 3-cyanopropyl | 3 | 3 | 1 | 7 |
| Example 25 | (Y) | allyl | [A]X=NH [A]X=NH | Formula (9) | [C]X=NH | 3-cyanopropyl | 3 | 3 | 1 | 7 |
| Example 26 | (Z) | allyl | [A]X=NH [A]X=NH | Formula (10) | [C]X=NH | 3-cyanopropyl | 3 | 3 | 1 | 7 |

Comparative Example 1

A compound represented by the following Formula (AA) was synthesized by the method described in Patent Document 3.

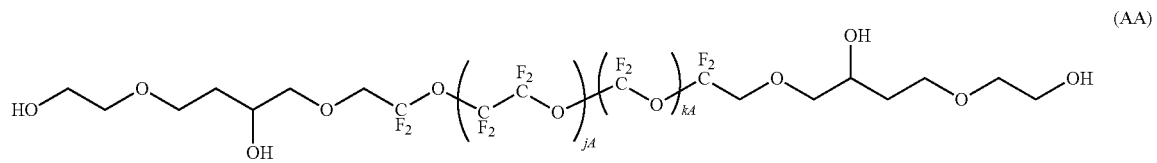

(AA)

(in Formula (AA), jA indicating the average degree of polymerization is 4.5, and kA indicating the average degree of polymerization is 4.5).

Comparative Example 2

The compound represented by the following Formula (AB) was synthesized by the method described in Patent Document 2.

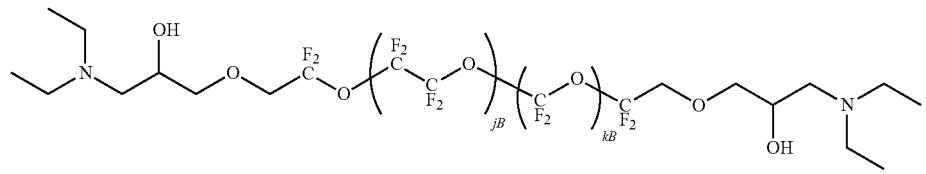

(in Formula (AB), jB indicating the average degree of polymerization is 4.5, and kB indicating the average degree of polymerization is 4.5).

Comparative Example 3

The compound represented by the following Formula (AC) was synthesized by the method described in Patent Document 1.

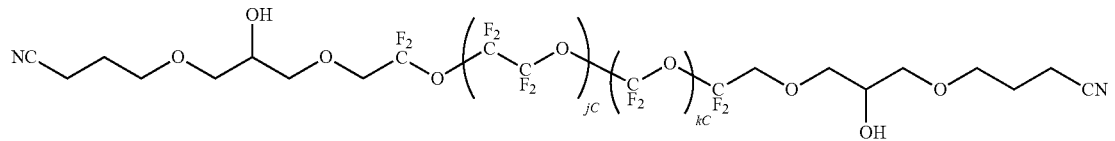

(in Formula (AC), jC indicating the average degree of polymerization is 4.5, and kC indicating the average degree of polymerization is 4.5).

The number-average molecular weight (Mn) of the compounds of Examples 1 to 26 and Comparative Examples 1 to 3 obtained in this manner was measured by the above method. The results are shown in Table 4.

TABLE 4

| | Number-average molecular weight | Compound | Film thickness (Å) | Friction coefficient increase time (sec) | Film thickness reduction rate (%) | Overall evaluation |
|---|---|---|---|---|---|---|
| Example 1 | 1280 | A | 8.5 | A | A | A |
| Example 2 | 1308 | B | 8.5 | A | A | A |
| Example 3 | 1280 | C | 8.5 | A | A | A |
| Example 4 | 1428 | D | 8.5 | B | A | B |
| Example 5 | 1454 | E | 8.5 | B | A | B |
| Example 6 | 1446 | F | 8.5 | B | A | B |
| Example 7 | 1428 | G | 8.5 | B | A | B |
| Example 8 | 1258 | H | 8.5 | B | A | B |
| Example 9 | 1374 | I | 8.5 | B | A | B |
| Example 10 | 1294 | J | 8.5 | A | A | A |
| Example 11 | 1424 | K | 8.5 | A | A | A |
| Example 12 | 1391 | L | 8.5 | A | A | A |
| Example 13 | 1265 | M | 8.5 | A | A | A |
| Example 14 | 1255 | N | 8.5 | A | A | A |
| Example 15 | 1319 | O | 8.5 | A | A | A |
| Example 16 | 1326 | P | 8.5 | A | A | A |
| Example 17 | 1363 | Q | 8.5 | A | A | A |
| Example 18 | 1429 | R | 8.5 | B | A | B |
| Example 19 | 1452 | S | 8.5 | B | A | B |
| Example 20 | 1480 | T | 8.5 | B | A | B |
| Example 21 | 1254 | U | 8.5 | A | A | A |
| Example 22 | 1429 | V | 8.5 | B | A | B |
| Example 23 | 1316 | W | 8.5 | A | A | A |
| Example 24 | 1351 | X | 8.5 | A | A | A |
| Example 25 | 1352 | Y | 8.5 | A | A | A |
| Example 26 | 1351 | Z | 8.5 | A | A | A |

TABLE 4-continued

|  | Number-average molecular weight | Compound | Film thickness (Å) | Friction coefficient increase time (sec) | Film thickness reduction rate (%) | Overall evaluation |
|---|---|---|---|---|---|---|
| Comparative Example 1 | 1266 | AA | 8.5 | D | D | D |
| Comparative Example 2 | 1260 | AB | 8.5 | D | D | D |
| Comparative Example 3 | 1232 | AC | 8.5 | C | D | D |

Next, a solution for forming a lubricating layer was prepared using the compounds obtained in Examples 1 to 26 and Comparative Examples 1 to 3 by the following method. Then, using the obtained solution for forming a lubricating layer, by the following method, a lubricating layer of the magnetic recording medium was formed to obtain magnetic recording media of Examples 1 to 26 and Comparative Examples 1 to 3.

"Solution for Forming Lubricating Layer"

The compounds obtained in Examples 1 to 26 and Comparative Examples 1 to 3 were each dissolved in Vertel (registered trademark) XF and diluted with Vertel (registered trademark) XF so that the film thickness when applied onto the protective layer was 8 to 9 Å, and thereby a solution for forming a lubricating layer was obtained.

"Magnetic Recording Medium"

A magnetic recording medium in which an adhesive layer, a soft magnetic layer, a first underlayer, a second underlayer, a magnetic layer and a protective layer were sequentially provided on a substrate having a diameter of 65 mm was prepared. The protective layer was made of carbon.

The solutions for forming a lubricating layer of Examples 1 to 26 and Comparative Examples 1 to 3 were applied onto the protective layer of the magnetic recording medium, in which respective layers up to the protective layer were formed, by a dipping method. Here, the dipping method was performed under conditions of an immersion speed of 10 mm/sec, an immersion time of 30 sec, and a lifting speed of 1.2 mm/sec.

Then, the magnetic recording medium to which the solution for forming a lubricating layer was applied was put into a thermostatic chamber at 120° C. and heated for 10 minutes to remove the solvent in the solution for forming a lubricating layer, and thus a lubricating layer was formed on the protective layer to obtain a magnetic recording medium.

(Film Thickness Measurement)

The film thickness of the lubricating layer of the magnetic recording media of Examples 1 to 26 and Comparative Examples 1 to 3 obtained in this manner was measured using FT-IR (product name: Nicolet iS50, commercially available from Thermo Fisher Scientific). The results are shown in Table 4.

Next, the following wear resistance test was performed on the magnetic recording media of Examples 1 to 26 and Comparative Examples 1 to 3.

(Wear Resistance Test)

Using a pin-on disc-type friction wear tester, an alumina sphere having a diameter of 2 mm as a contact was slid on the lubricating layer of the magnetic recording medium at a load of 40 gf and a sliding speed of 0.25 m/sec, and the friction coefficient of the surface of the lubricating layer was measured. Then, the sliding time until the friction coefficient of the surface of the lubricating layer sharply increased (friction coefficient increase time) was measured. The friction coefficient increase time was measured four times for the lubricating layer of each magnetic recording medium, and the average value (time) thereof was used as an index of the wear resistance of a lubricant coating.

Table 4 shows the results of the friction coefficient increase time of the magnetic recording media using the compounds of Examples 1 to 26 and the compounds of Comparative Examples 1 to 3. The friction coefficient increase time was evaluated as follows. It is understood that a larger value of the friction coefficient increase time indicates better results.

A (excellent): 750 sec or longer
B (good): 650 sec or longer and shorter than 750 sec
C (acceptable): 550 sec or longer and shorter than 650 sec
D (unacceptable): shorter than 550 sec Here, the time until the friction coefficient sharply increased can be used as an index of the wear resistance of the lubricating layer for the following reasons. This is because wear of the lubricating layer of the magnetic recording medium proceeds when the magnetic recording medium is used, and when the lubricating layer disappears due to wear, the contact and the protective layer come into direct contact with each other, and the friction coefficient sharply increases. The time until the friction coefficient sharply increased is thought to be correlated with the friction test.

(Spin-Off Characteristic Test)

A magnetic recording medium was mounted on a spin stand, and rotated at a rotational speed of 10,000 rpm for 72 hours in an environment of 80° C. Before and after this operation, the film thickness of the lubricating layer at a position with a radius of 20 mm from the center of the magnetic recording medium was measured using FT-IR, and the film thickness reduction rate of the lubricating layer before and after the test was calculated. Using the calculated film thickness reduction rate, based on the following evaluation criteria, spin-off characteristics were evaluated. The results are shown in Table 4.

"Evaluation Criteria for Spin-Off Characteristics"

A (excellent): a film thickness reduction rate of 2% or less
B (good): a film thickness reduction rate of more than 2% and 3% or less
C (acceptable): a film thickness reduction rate of more than 3% and 9% or less
D (unacceptable): a film thickness reduction rate of more than 9%

(Overall Evaluation)

From the results of the wear resistance test and the spin-off characteristic test, based on the following criteria, overall evaluation was performed.

A (excellent): the wear resistance test and the spin-off characteristic test were all evaluated as A.
B (good): the wear resistance test and the spin-off characteristic test were evaluated as A or B, and either of the wear resistance test and the spin-off characteristic test was evaluated as B.

D (unacceptable): the above criteria for A (excellent) and B (good) were not satisfied.

As shown in Table 4, the magnetic recording media of Examples 1 to 26 had a longer sliding time until the friction coefficient sharply increased and better wear resistance than the magnetic recording media of Comparative Examples 1 to 3. In addition, the magnetic recording media of Examples 1 to 26 had better spin-off characteristics (film thickness reduction rate) than the magnetic recording media of Comparative Examples 1 to 3.

This is speculated to be due to the inclusion of a compound in which at least one of $R^2$ and $R^4$ in Formula (1) contains one or more secondary amine structures, and at least one of $R^1$—$R^2$— and —$R^4$—$R^5$ contains one or more cyano groups in the lubricating layer of the magnetic recording media of Examples 1 to 26.

In addition, the magnetic recording media of Examples 1 to 3, 10 to 17, 21, and 23 to 26 using the compounds (A) to (C), (J) to (Q), (U), and (W) to (Z) had a good overall evaluation result of A (excellent). In the compounds (A) to (C), (J) to (Q), (U), and (W) to (Z), the number of secondary amine structures (—NH—) contained in the molecule was 2 or more, the number of hydroxyl groups was 3 or less, the number of cyano groups was 3 or less, and the total number of secondary amine structures, hydroxyl groups and cyano groups was 8 or less.

INDUSTRIAL APPLICABILITY

When the lubricant for a magnetic recording medium containing the fluorine-containing ether compound of the present invention is used, it is possible to form a lubricating layer having excellent wear resistance and spin-off resistance even if the thickness thereof is thin.

That is, according to the present invention, it is possible to form a lubricating layer having excellent wear resistance and spin-off resistance even if the thickness is thin, and it is possible to provide a fluorine-containing ether compound suitable as a material for a lubricant for a magnetic recording medium.

REFERENCE SIGNS LIST

10 Magnetic recording medium
11 Substrate
12 Adhesive layer
13 Soft magnetic layer
14 First underlayer
15 Second underlayer
16 Magnetic layer
17 Protective layer
18 Lubricating layer

The invention claimed is:

1. A fluorine-containing ether compound represented by Formula (1) shown below:

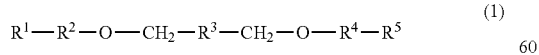

(in Formula (1), $R^3$ is a perfluoropolyether chain; $R^1$ and $R^5$ are each independently a terminal group composed of either an alkyl group which may have a substituent or a hydrocarbon group having a double bond or triple bond; $R^2$ and $R^4$ are each a divalent linking group containing one or more heteroatoms and have one or more polar groups, and a terminal end thereof on the side bonded to $R^1$ and $R^5$ is a heteroatom; at least one of $R^2$ and $R^4$ contains one or more secondary amine structures; and at least one of $R^1$-$R^2$— and —$R^4$-$R^5$ contains one or more cyano groups).

2. The fluorine-containing ether compound according to claim 1,
wherein the polar groups of $R^2$ and $R^4$ are any one selected from a secondary amine structure, a hydroxyl group and a cyano group.

3. The fluorine-containing ether compound according to claim 1,
wherein, in Formula (1), —$R^2$—O— is represented by Formula (2) shown below, and —O—$R^4$— is represented by Formula (3) shown below:

(in Formula (2), [A] is represented by Formula (4-1) shown below, and [B] is represented by Formula (4-2) shown below; the order of [A] and [B] in Formula (2) may be interchanged; a is an integer of 0 to 3, d is an integer of 0 to 3, at least one of a and d is 1 or more; and a terminal —$CH_2$— located on the side opposite to X in Formula (4-1) or a terminal —$CH_2$— located on the side opposite to X in (4-2) is bonded to —O— in Formula (2))

(in Formula (3), [C] is represented by Formula (5-1) shown below, and [D] is represented by Formula (5-2) shown below; the order of [C] and [D] in Formula (3) may be interchanged; g is an integer of 0 to 3, j is an integer of 0 to 3, and at least one of g and j is 1 or more; and a terminal —$CH_2$— located on the side opposite to X in Formula (5-1) or a terminal —$CH_2$— located on the side opposite to X in (5-2) is bonded to —O— in Formula (3))

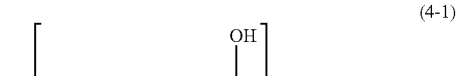
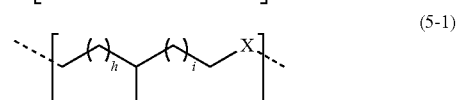
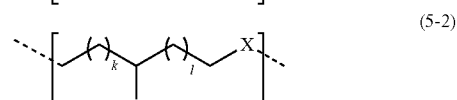

(in Formula (4-1), b and c are each an integer of 0 to 4; in Formula (4-2), e and f are each an integer of 0 to 4; in Formula (5-1), h and i are each an integer of 0 to 4; in Formula (5-2), k and l are each an integer of 0 to 4; in Formulae (4-1), (4-2), (5-1), and (5-2), X is O or NH; and one or more of X's in Formulae (4-1), (4-2), (5-1), and (5-2) are NH).

4. The fluorine-containing ether compound according to claim 1,
wherein the number of secondary amine structures contained in a molecule thereof is 2 or more.

5. The fluorine-containing ether compound according to claim 1,
wherein the number of hydroxyl groups contained in a molecule thereof is 3 or less.

6. The fluorine-containing ether compound according to claim 1,
wherein the number of cyano groups contained in a molecule thereof is 3 or less.

7. The fluorine-containing ether compound according to claim 1,
wherein a total number of secondary amine structures, hydroxyl groups and cyano groups contained in the molecule is 8 or less.

8. The fluorine-containing ether compound according to claim 1,
wherein the number of secondary amine structures contained in a molecule thereof is 2 or more, the number of hydroxyl groups is 3 or less, the number of cyano groups is 3 or less, and a total number of secondary amine structures, hydroxyl groups and cyano groups is 8 or less.

9. The fluorine-containing ether compound according to claim 1,
wherein —R²—O— in Formula (1) is any of Formulae (11-1) to (11-12) shown below:

 (11-1)

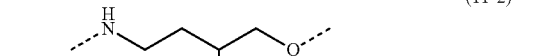 (11-2)

 (11-3)

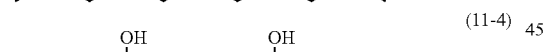 (11-4)

 (11-5)

 (11-6)

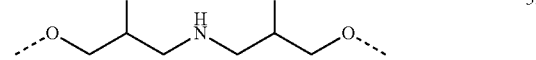 (11-7)

 (11-8)

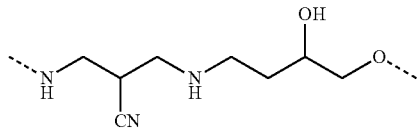 (11-9)

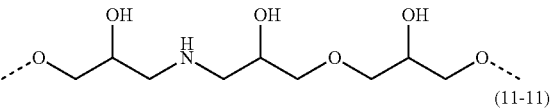 (11-10)

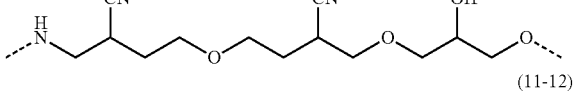 (11-11)

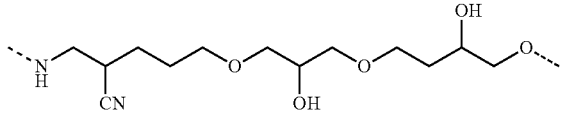 (11-12)

10. The fluorine-containing ether compound according to claim 1,
wherein the alkyl group which may have a substituent is an alkyl group having a hydroxyl group or cyano group.

11. The fluorine-containing ether compound according to claim 1,
wherein the hydrocarbon group having a double bond or triple bond is any of a group containing an aromatic hydrocarbon, a group containing an aromatic heterocycle, an alkenyl group, and an alkynyl group.

12. The fluorine-containing ether compound according to claim 1,
wherein R³ in Formula (1) is any of Formulae (6) to (10) shown below:

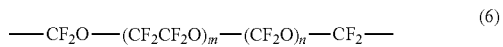 (6)

(in Formula (6), m and n indicate an average degree of polymerization, and each represent 0.1 to 30)

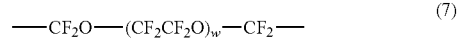 (7)

(in Formula (7), w indicates an average degree of polymerization, and is 0.1 to 30)

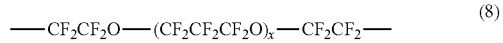 (8)

(in Formula (8), x indicates an average degree of polymerization, and is 0.1 to 30)

 (9)

(in Formula (9), y indicates an average degree of polymerization, and is 0.1 to 30)

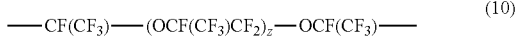 (10)

(in Formula (10), z indicates an average degree of polymerization, and is 0.1 to 30).

13. The fluorine-containing ether compound according to claim 1,
wherein the compound represented by Formula (1) is any one of compounds represented by Formulae (A), (J), (P), (Q) and (U) shown below:

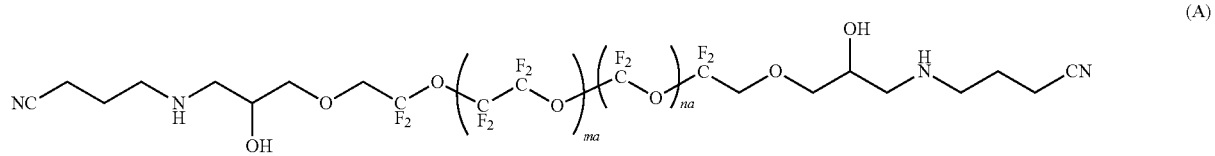

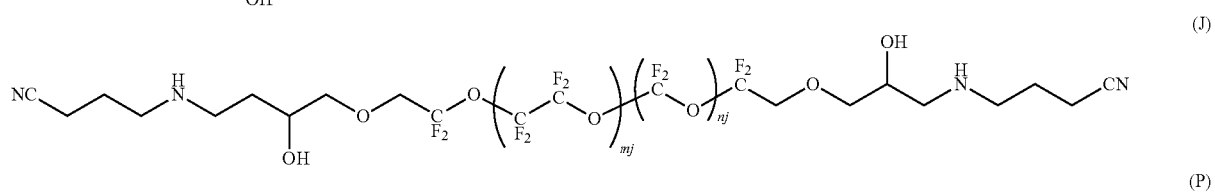

(in Formula (A), ma and na indicate an average degree of polymerization, ma is 1 to 30, and na is 0.1 to 30)
(in Formula (J), mj and nj indicate an average degree of polymerization, mj is 1 to 30, and nj is 0.1 to 30)
(in Formula (P), mp and np indicate an average degree of polymerization, mp is 1 to 30, and np is 0.1 to 30)

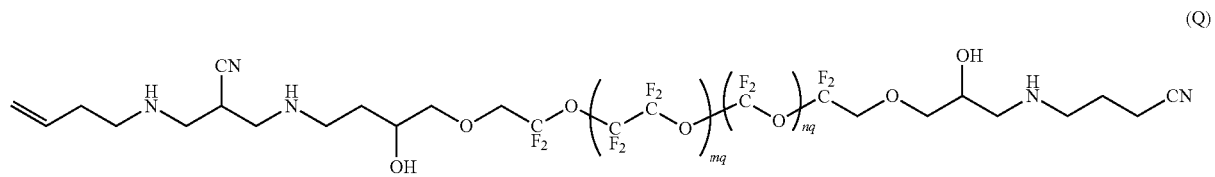

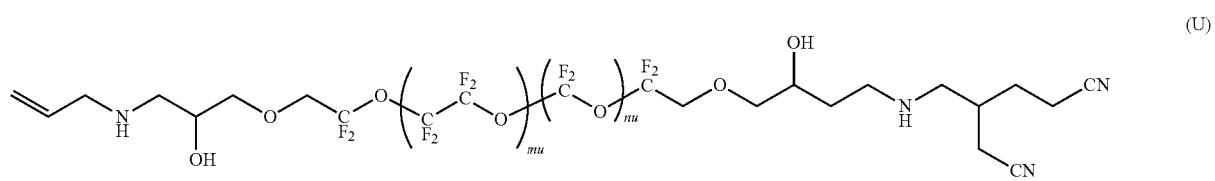

(in Formula (Q), mq and nq indicate an average degree of polymerization, mq is 1 to 30, and nq is 0.1 to 30)
(in Formula (U), mu and nu indicate an average degree of polymerization, mu is 1 to 30, and nu is 0.1 to 30).

14. The fluorine-containing ether compound according to claim 1,
wherein a number-average molecular weight thereof is in a range of 500 to 10,000.

15. A lubricant for a magnetic recording medium, which contains the fluorine-containing ether compound according to claim 1.

16. A magnetic recording medium in which at least a magnetic layer, a protective layer and a lubricating layer are sequentially provided on a substrate,
wherein the lubricating layer contains the fluorine-containing ether compound according to claim 1.

17. The magnetic recording medium according to claim 16,
wherein the lubricating layer has an average film thickness of 0.5 nm to 2.0 nm.

* * * * *